US012257356B2

(12) United States Patent
Hankerson

(10) Patent No.: US 12,257,356 B2
(45) Date of Patent: Mar. 25, 2025

(54) SYSTEMS AND METHODS FOR APPLYING ANTIMICROBIAL HAND BARRIER

(71) Applicant: Rachel Hankerson, Florissant, MO (US)

(72) Inventor: Rachel Hankerson, Florissant, MO (US)

( * ) Notice: Subject to any disclaimer, the term of this patent is extended or adjusted under 35 U.S.C. 154(b) by 232 days.

(21) Appl. No.: 17/208,915

(22) Filed: Mar. 22, 2021

(65) Prior Publication Data

US 2021/0290801 A1    Sep. 23, 2021

Related U.S. Application Data

(60) Provisional application No. 63/126,929, filed on Dec. 17, 2020, provisional application No. 62/992,680, filed on Mar. 20, 2020.

(51) Int. Cl.
*A61L 2/18* (2006.01)

(52) U.S. Cl.
CPC ............. *A61L 2/18* (2013.01); *A61L 2202/15* (2013.01)

(58) Field of Classification Search
CPC . A61L 2/18; A61L 2/24; A61L 2/0088; A61L 26/0076; A61L 2202/14; A61L 2202/15; A61B 42/00; B05D 5/00; A47K 5/12; A47K 5/1217; B29D 99/0067
See application file for complete search history.

(56) References Cited

U.S. PATENT DOCUMENTS

| | | | | | |
|---|---|---|---|---|---|
| 2,814,069 | A | * | 11/1957 | Lenhart | B29C 41/14 425/269 |
| 3,268,647 | A | * | 8/1966 | Hayes | B29C 41/40 264/303 |
| 3,397,265 | A | * | 8/1968 | Ansell | B29C 41/14 264/306 |
| 3,757,806 | A | * | 9/1973 | Bhaskar | A61C 17/028 134/191 |
| 3,843,296 | A | * | 10/1974 | Sidley | B29D 99/0067 264/306 |
| 4,335,833 | A | * | 6/1982 | Arabian | A47K 5/12 222/23 |
| 5,041,287 | A | * | 8/1991 | Driggers | A61L 26/0095 424/47 |
| 5,135,721 | A | * | 8/1992 | Richard | A61L 2/24 425/269 |
| 5,554,673 | A | * | 9/1996 | Shah | A61F 6/04 524/113 |
| 5,632,727 | A | * | 5/1997 | Tipton | A61K 9/7015 604/890.1 |
| 7,449,194 | B2 | | 11/2008 | Lelah et al. | |
| 8,343,523 | B2 | | 1/2013 | Toreki et al. | |

(Continued)

*Primary Examiner* — Jennifer Wecker
*Assistant Examiner* — Brady C Pilsbury
(74) *Attorney, Agent, or Firm* — Armstrong Teasdale LLP

(57) ABSTRACT

Systems and methods for applying an antimicrobial barrier to a hand include a barrier precursor material, a reservoir for the barrier precursor material, and a dispenser connected to the reservoir and configured to dispense the barrier precursor material onto a hand positioned adjacent the dispenser. The barrier precursor material cures and adheres to the hand to form an antimicrobial barrier on the hand. The antimicrobial barrier does not retain or transfer microorganisms from an object grasped by the hand.

20 Claims, 17 Drawing Sheets

(56) References Cited

U.S. PATENT DOCUMENTS

| | | | | |
|---|---|---|---|---|
| 8,932,664 | B2* | 1/2015 | Bengtson | B29C 41/00 |
| | | | | 427/430.1 |
| 9,750,755 | B2 | 9/2017 | Ahmed et al. | |
| 9,782,514 | B2* | 10/2017 | Hardy | A61L 26/0052 |
| 2004/0073186 | A1* | 4/2004 | Cameron | A61M 35/25 |
| | | | | 604/389 |
| 2005/0081291 | A1* | 4/2005 | Otten | A61B 90/80 |
| | | | | 4/621 |
| 2007/0213877 | A1* | 9/2007 | Hart | G07C 9/22 |
| | | | | 700/282 |
| 2013/0309128 | A1* | 11/2013 | Voegeli | A61L 2/22 |
| | | | | 422/3 |
| 2016/0309967 | A1* | 10/2016 | Pelfrey | A47K 5/1217 |
| 2016/0339132 | A1* | 11/2016 | Cosman | F26B 9/003 |
| 2017/0296485 | A1* | 10/2017 | Kottayil | A61K 47/22 |
| 2018/0214588 | A1* | 8/2018 | Casares | A61L 2/202 |
| 2019/0172336 | A1* | 6/2019 | Haidegger | A61L 2/0088 |

* cited by examiner

SYSTEMS AND METHODS FOR APPLYING ANTIMICROBIAL HAND BARRIER

CROSS-REFERENCE TO RELATED APPLICATIONS

This application claims priority to U.S. Provisional Application No. 63/126,929, filed Dec. 17, 2020 and U.S. Provisional Application No. 62/992,680, filed Mar. 20, 2020, the contents of which are incorporated herein by reference in their entirety.

BACKGROUND

The field of the disclosure relates generally to hand barrier systems and methods and, more particularly, to systems and methods for applying antimicrobial barriers onto hands.

Germs, bacteria, diseases, and other materials are spread from person to person through people's hands. For example, germs may be transmitted when people contact each other or when people contact objects that have microorganisms on them. Frequent hand washing and/or sanitizing may reduce the transmission of microorganisms by removing the microorganisms after the hand has picked up microorganisms. However, people may not always have access to materials to wash their hands and/or may not wish to take the time to wash their hands. In addition, people may transfer the microorganisms to themselves, objects, or other people prior to washing or sanitizing their hands. Moreover, some soaps or sanitizers include harsh chemicals that can irritate or dry out skin.

In particular, diseases such as the novel coronavirus 2019 (COVID-19) have been transmitted when people socially interact or otherwise engage in necessary public activities such as working, shopping, eating, exercising, and any other activities. Accordingly, during the COVID-19 pandemic, handwashing, social distancing, and other measures have been seen as vital to controlling the spread of disease. However, these measures are not 100% effective in reducing the transmission of germs. Moreover, there are situations where the measures are difficult to enact. For example, some people work in fields where it is not possible to avoid contact with individuals who may have the virus. In addition, some people would like to utilize measures which are not seen as obtrusive and can allow the people to participate in social activities safely.

People typically use their hands to perform numerous tasks throughout each day and repeatedly contact surfaces that may contain germs. For example, many people use their hands to touch objects such as doors, serving utensils, gas pumps, keyboards, tables, chairs, currency, faucets, and even other people's hands. After touching one or more of these objects, people may then touch their face and, as a result, become infected. Often, these actions are carried out subconsciously and without adequate protection. Sometimes, people wear gloves that are either disposable or reusable. Reusable gloves can be expensive and are cumbersome for some wearers. At least some disposable gloves are non-biodegradable and generate permanent waste. Also, disposable gloves often include materials such as latex that can irritate skin and/or cause allergic reactions. In addition, gloves may hinder the wearer's ability to operate a touch screen or portable electronic device such as a smart phone. Moreover, the gloves still pick up, retain, and transfer microorganisms. For example, the wearer may transfer the microorganisms to themselves when they contact the outside of the glove for removal and may transfer the microorganisms to other people or surfaces that they contact while wearing the gloves.

Accordingly, there is a need for systems and methods to provide barriers to reduce the transmission of microorganisms.

BRIEF DESCRIPTION

In one aspect, a system for applying an antimicrobial barrier to a hand includes a barrier precursor material, a reservoir for the barrier precursor material, and a dispenser connected to the reservoir and configured to dispense the barrier precursor material onto a hand positioned adjacent the dispenser. The barrier precursor material cures and adheres to the hand to form an antimicrobial barrier on the hand. The antimicrobial barrier does not retain or transfer microorganisms from an object grasped by the hand.

In another aspect, a method of applying an antimicrobial barrier to a hand includes detecting a hand positioned adjacent a dispenser connected to a reservoir of barrier precursor material and dispensing, via the dispenser, the barrier precursor material onto the hand positioned adjacent the dispenser. The barrier precursor material cures and adheres to the hand to form an antimicrobial barrier on the hand after the barrier precursor is dispensed onto the hand by the dispenser. The antimicrobial barrier does not retain or transfer microorganisms from an object grasped by the hand.

In yet another aspect, a hand barrier comprises an antimicrobial material that adheres to and covers a hand. The antimicrobial material does not retain or transfer microorganisms from an object grasped by the hand.

DETAILED DESCRIPTION

Figure 1:
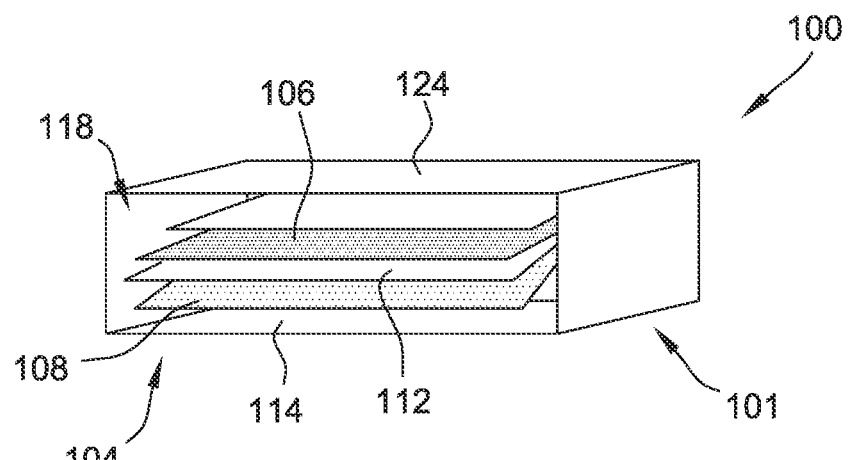
FIG. 1 is a schematic view of a system for dispensing a hand barrier.

The hand barrier provided by the methods and systems described herein can reduce the spread of microorganisms of bacteria, germs, and other virus causing pathogens that are transferred through touch. Accordingly, the systems and methods described herein may help keep people healthier, reduce the burden on the healthcare system, and provide a means to combat pandemics such as COVID-19. In contrast to cleaning solutions such as hand sanitizer which are used to remove a percentage of the bacteria and germs that have already been picked-up on the hands, the hand barrier is anti-microbial and covers the hand to prevent the hand from contacting, retaining, or transferring microorganisms such as germs or bacteria. The hand barrier reduces or eliminates the risk of picking up, retaining, or transferring germs/bacteria. In contrast, gloves only protect the hand inside the glove from bacteria and germs while the gloves are on the hand. The outside of the glove normally picks-up, retains, and transmits germs which may be transferred to the hand upon removal and/or be transferred to another person or surface when the outside of the glove contacts the person or surface.

Embodiments include a biodegradable antimicrobial spray polymer that would cover the user's hand and prevent the attraction, retention, and transfer of bacteria, or any other virus causing pathogens that are normally associated with touch. The spray polymer is a liquid based solution that would be applied (e.g., sprayed) onto the user's hand from a dispenser, curing in less than 2 seconds. The solution is antimicrobial. As used herein, the term "antimicrobial" refers to a material that kills or stops the spread of microorganisms such as bacteria and germs.

Accordingly, the described systems and methods allow people to pick up, contact, or otherwise use objects without risk of retaining or transferring microorganisms. For example, the hand barrier kills or stops the transfer of microorganisms when the hand barrier contacts a surface that includes microorganisms and the wearer does not retain or transfer the microorganisms after touching the surface. Accordingly, the wearer may contact a public surface or object such as a gas pump, a shopping cart, a touchscreen on a display or payment center, or any other public item and not transfer microorganisms or become sick because of the microorganism if the wearer eats or performs other actions after touching the surface that has microorganisms.

In some embodiments, the system includes a dispenser that is mounted in a public place such as a gas station or a grocery store and a person may place his/her hand in the dispenser to have hand barriers applied to the hands. The system includes a device that would identify the hand, measure the hand, scan the hand, spray the hand with a biodegradable solution, and cure the solution within less than 2 seconds. The customer would remove their hand from the dispenser, with the affixed barrier on the hand. The hand barrier would allow him/her to touch a gas pump, pull a door handle, push a shopping cart, use medical devices, hold on to an escalator hand rail, contact objects in hospitals or clinics, contact a patient bed, use medical and non-medical instruments, grasp tools, contact infrastructure, and/or contact any other public object without picking-up, retaining, or transferring microorganisms. The customer can wash off the hand barrier or peel it off.

Example embodiments of systems and methods for dispensing hand barriers include a dispenser that is configured to dispense a disposable barrier. The barrier is configured to attach to the hand and is sized and shaped to conform to and cover the hand of the wearer. For example, in some embodiments, the barrier is formed from a biodegradable paper and/or a solution. The biodegradable paper may include an adhesive that attaches to the hand. In some embodiments, the hand barrier is formed from a solution that is configured to adhere to the hand and then dry or cure on the hand in less than two seconds to form the barrier. In some embodiments, the dispenser includes one or more sensors that are configured to detect the hand and allow the dispenser to determine a size or amount of barrier required to cover the hand.

The methods and systems described herein would help to minimize the spread of bacteria from the many uses of the hand. For example, the system and methods would form a protective cover over the palm, fingers, and/or entire hand of users, i.e., a hand barrier. The hand barrier can reduce the transmission of bacteria by the hand throughout the day.

In embodiments, the hand barrier covers the entire palm and fingers of the human hand. The hand barriers may be sized and shaped to accommodate different hand sizes and body types. For example, the hand barrier may be used to protect the hand at the gas station when touching a gas pump to insert fuel into a vehicle. During surgery; the hand barrier would mitigate the transfer of germs from the surgical instruments to the body. The hand barrier can also reduce the transmission of bacteria and germs when hands are used to open doors, grasp serving utensils, pump gas, push shopping carts in stores, and touch handrails and door knobs. The hand barrier may be used in public or private locations such as hospitals, schools, houses, public transportation, restrooms, theaters, cliques, and in any other venues where one would like to protect their hand from what he/she touches.

Embodiments of the system and methods incorporate both software and hardware components.

In some embodiments, the hand barrier provides a temporary protection for a hand (right or left) and the hand barrier is fitted to the hand. For example, a hand (right or left) may be scanned, a controller may determine a size and fit required for protection, and the hand barrier may be formed to fit the scanned hand. The hand (right or left) may be inserted into a scanner and the scanner may outline the hand. Suitably, sensors are positioned within the scanner to identify and measure the hand without the scanner contacting the hand. The system then tailors a hand barrier based on the outline of hand. The system may then dispense the hand barrier onto the hand such that the hand barrier covers the hand. The hand barrier may include adhesive that adheres to the hand. In some embodiments, the hand barrier is biodegradable and can be easily pulled off or washed off after use.

A hand barrier can be applied to the palm, fingers, a portion of a wrist, and/or the entirety of the hand in different ways, some of which include:

a. Place the hand(s) into a housing and/or adjacent a dispenser. The dispenser may be configured to detect at least one characteristic of the hand and dispense a solution (e.g., a gel) onto the face/front of the hand, palm, fingers, thumb, a portion of wrist, and/or the entire hand. The gel may dry to form a hand barrier.
b. Place the hand(s) into a hand barrier device. The device can scan the hand and create a hand barrier that is shaped to fit the hand. The hand barrier is placed onto the face/front of the hand, palm, fingers, thumb, a portion of wrist, and/or the entire hand. The hand barrier would cure and be secured to the hand.
c. Provide a box of ready-made hand barriers that have different variations of hand sizes outlined (like a sewing pattern). Each hand barrier would be enclosed by a protective release sheet which would prevent contamination of the hand barrier prior to use. A wearer would align his/her hand on the protected sheet with the patterned outline. The wearer could choose the outline that is closest to the size of his/her hand. The wearer would then peel his/her size away from the remaining patterns, allowing him/her to discard whatever is left over. Each protected ready-made hand barrier would be boxed and sold according to size, such as: for infants, children, teenagers, and adults. Alternatively, a package of precut hand-shaped sheets may be sold in different sizes. In use, a wearer receives a package of hand barriers and peels the hand barriers off one at a time for use, with no cutting necessary.
d. Provide a box of ready-made protective sheets, without a pattern/design. The wearer would also have a stylus/marker, plain protected sheets, and a substrate (e.g., cardboard). The wearer would first lay the substrate on a flat surface and place the protected sheet on top of the substrate. The wearer then would place his/her hand on the substrate and the protective sheet, trace the outline of his/her hand onto the protective sheet, cut the outline of the hand from the protective sheet, peel back a top protected cover from the sheet, place his/her hand on an adhesive side of the sheet, and pull the base of the cover away from the sheet
e. Provide personal-use containers. The containers may include a quantity of the solution that can be dispensed onto the hand to form the hand barriers. The containers may be sized for convenient use by people in the homes, workstations, and/or any other suitable location. In some embodiments, the containers may be sized for the user to store in a pocket, purse, or other convenient storage means for transporting the container.

Figure 2:
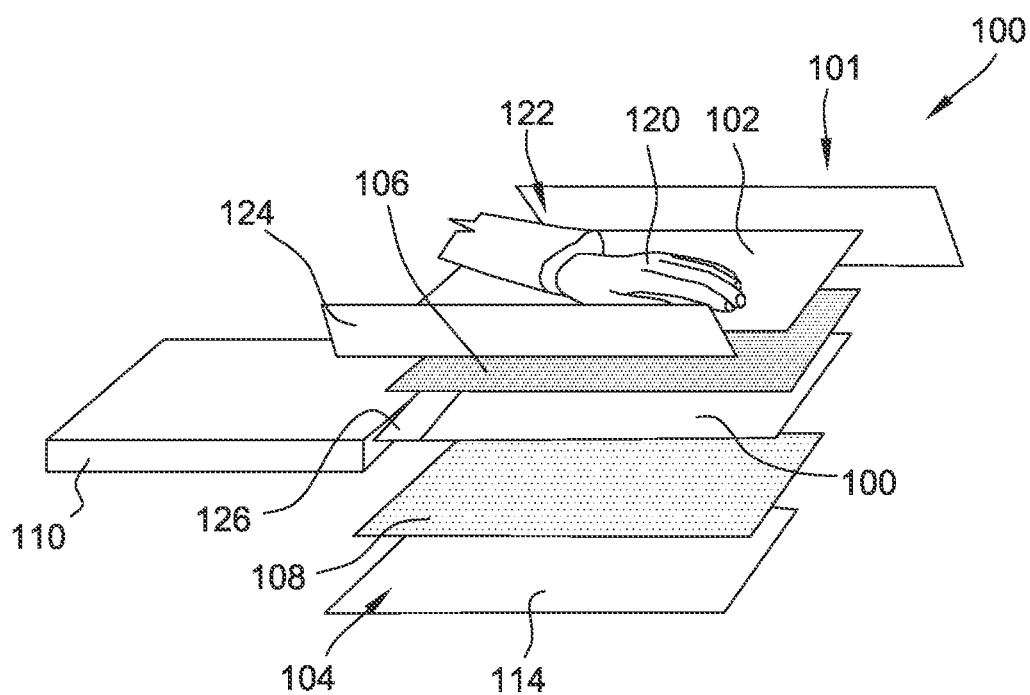
FIG. 2 is a schematic, partially exploded view of the system shown in FIG. 1, where a housing of the system is in an open position.
Figure 3:
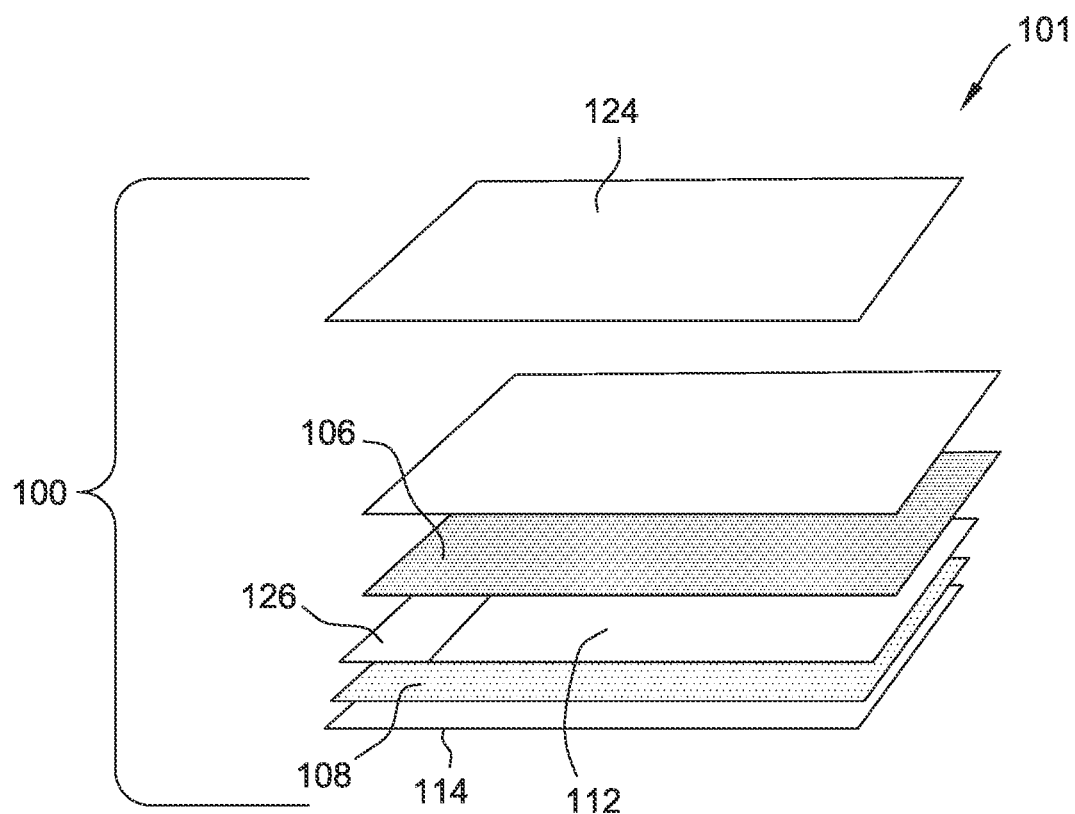
FIG. 3 is a schematic view of the system of FIGS. 1 and 2 with the housing in a closed position.
Figure 4:
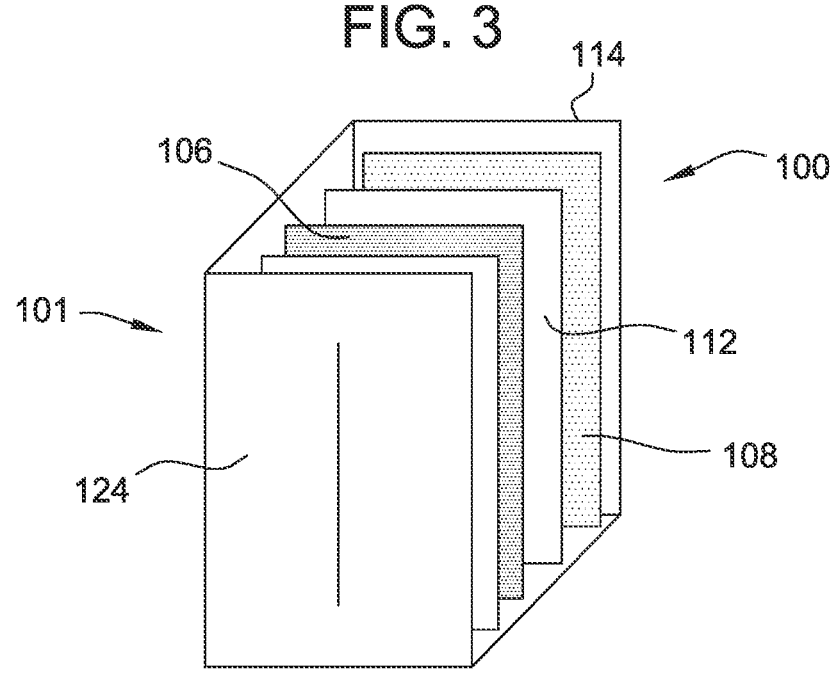
FIG. 4 is a schematic view of a portion of the system of FIG. 1.

FIG. 1 is a schematic view of a system 100 for dispensing a hand barrier 102. FIG. 2 is a schematic view of the system 100 with a housing 104 in an open position. FIGS. 3 and 4 are schematic views of the system 100 with the housing 104 in a closed position. The system 100 includes a dispenser 101, a controller 108, and a reservoir 110. The dispenser 101 may include a housing 104 and a sensor 106. In other embodiments, the system 100 may include any components that enable the system to operate as described herein.

The dispenser 101 is connected to the reservoir 110 (shown in FIG. 2) of a barrier precursor material 112. The reservoir 110 may include a container shaped to hold a stack of sheets of the barrier precursor material 112 and/or may include a tank configured to hold a liquid or semi-liquid material. The reservoir 110 is sealed from the outer environment to prevent the barrier precursor material 112 from being contaminated. In some embodiments, the reservoir 110 includes temperature, humidity, and/or any suitable environmental controls to provide a desired environment for the barrier precursor material 112. For example, in some embodiments where the barrier precursor material 112 is a liquid or semi-liquid the system 100 may include a heat exchanger configured to maintain the barrier precursor material 112 at a temperature selected to maintain the barrier precursor material 112 in a desired state.

The housing 104 includes at least one wall 114. For example, the housing 104 includes a bottom wall 114 and side walls (not shown in FIGS. 1 and 2) collectively defining an interior space 118 sized to receive a hand 120. The housing 104 also defines an opening 122 for the hand to be positioned through and into the interior space 118. The opening 122 is selectively covered by a cover or door 124. The door 124 is positionable between an open position (shown in FIG. 1) and a close position (shown in FIG. 2). For example, the door 124 may include one or more rotatable or slidable panels. The controller 108 may move the door 124 between the open position and close position based on information from a user interface. For example, the user interface may include a payment module which processes user payments. Accordingly, the door 124 may restrict access to the hand barriers 102 based on criteria stored in the controller 108 (e.g., payment status or user credentials). In addition, the door 124 seals the interior space 118 from the exterior environment to reduce exposure of the components within the housing 104 to the external environment.

The sensor 106 is configured to detect at least one characteristic of the hand 120. For example, the sensor 106 may include a proximity sensor that detects the hand 120 when the hand 120 is adjacent the housing 104 and/or when the hand 120 is within the interior space 118. In the illustrated embodiment, the sensor 106 includes a scanner that is configured to generate an image of the hand 120 including an outline of the hand 120. The image of the hand 120 depicts the shape and size of the hand 120. In other embodiments, the sensor 106 may include one or more of the following sensors: an infrared sensor, a temperature sensor, a moisture sensor, and any other suitable sensor.

The controller 108 is connected to the sensor 106 and is configured to receive information from the sensor 106. The controller 108 is configured to determine characteristics of the hand 120 based on the information from the sensor 106. For example, the controller 108 may determine the size and shape of the hand 120 from an image received from the scanner and determine a suitable size and shape of the hand barrier 102 based on the image of the hand 120. In some embodiments, the controller 108 controls components of the system 100 such as the door 124 based on information from the sensor 106. For example, the controller 108 may cause the door 124 to move to the open position when the sensor 106 detects that the hand 120 is adjacent the housing 104.

In some embodiments, the dispenser 101 may include a suitable ejector mechanism configured to eject the barrier precursor material and/or the hand barrier. For example, the dispenser 101 may include a nozzle, an actuator, a positionable tray, a conveyor, and/or a roller. In the example, the dispenser 101 includes a feed conveyor 126 to move the barrier precursor materials from the reservoir 110 into position within the housing 104. The feed conveyor 126 may facilitate the hand barrier attaching to the hand 120 by properly aligning the barrier precursor material within the housing 104. In addition, the feed conveyor 126 may provide a seal or closure that maintains the barrier precursor materials in the reservoir 110 and protects the barrier precursor materials from exposure.

During operation, individuals can place there hand into the interior space 118 through the opening 122. The sensor 106 detects a characteristic of the hand 120 and the controller 108 selects a barrier based on the characteristic. The barrier is then applied to and adheres to the hand. The dispenser 101 may be connected to an external power supply and/or include an internal power source. For example, the dispenser 101 may include a battery with at least a 10 year service life.

The controller 108 is configured to operate the dispenser 101 in accordance with instructions stored, for example, on a memory. For example, the controller 108 is configured to process payments, open/close the door 124, operate a scanner of the sensor 106 to scan the hand 120, operate a the dispenser 101 to fabricate the hand barrier, and/or operate the dispenser 101 to cut the hand barrier to match the shape of the hand 120.

In some embodiments, the controller 108 receives and stores information relating to the operation of the system 100. For example, the controller 108 may determine and/or store the number of hands scanned per day, the amount of solution that has been dispensed, the amount of solution that remains in the reservoir 110, an estimated number of hands that can be covered with the remaining solution, an estimated battery life, maintenance information for the dispenser 101, and/or any other operating parameters. The controller 108 may cause the information to be displayed on a user interface and/or the controller 108 may send the information to a remote computing device. For example, the controller 108 automatically sends an alert to a computing device associated with a person responsible for maintaining the system 100 when the reservoir 110 reaches a certain level and/or maintenance is required.

Figure 5:
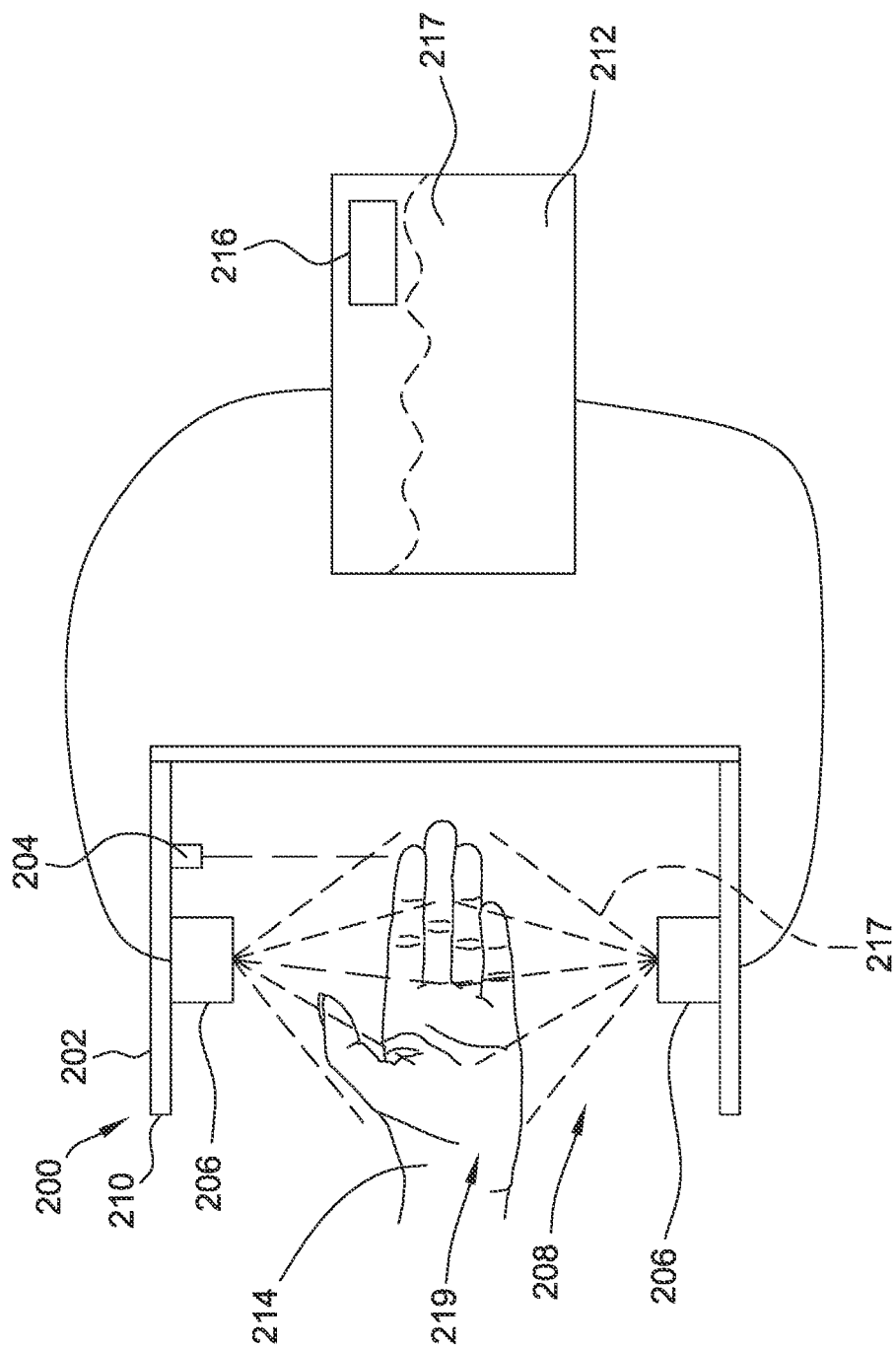
FIG. 5 is a schematic view of an alternative embodiment of a dispenser for use with the system of FIG. 1.

FIG. 5 is a schematic view of an alternative embodiment of a dispenser 200 for use with the system 100 (shown in FIG. 1). Dispenser 200 includes a housing 202, at least one sensor 204, and at least one nozzle 206. The housing 202 defines an interior space 208 and an opening 210 into the interior space. The sensor 204 and/or the nozzles 206 may be mounted to the housing 202. In the example, two nozzles 206 are mounted to opposite walls of the housing 202. The sensor 204 is positioned within the interior space 208 on the side of the nozzles 206 opposite the opening 210. Accordingly, the sensor 204 detects when the hand is inserted into the interior space 208 beyond the nozzles 206.

The nozzles 206 are connected to at least one reservoir 212 and configured to receive liquid barrier precursor material 217 from the reservoir. The nozzles 206 spray the liquid barrier precursor material 217 onto a hand 214 positioned within the interior space 208. In less than 2 seconds, the liquid barrier precursor material 217 forms a barrier 219 on the hand 214. In some embodiments, the housing 202 may include lights, heat sources, fans, gas supplies, or other mechanisms to help the liquid barrier precursor material 217 dry and form the hand barrier 219.

During use, a person positions their hand 214 within the interior space 208 of the housing 202 and the sensor 204 detects the hand 214. The sensor 204 may include any suitable sensor including, without limitation, a proximity sensor, an infrared sensor, a temperature sensor, and/or a moisture sensor. The dispenser 200 determines at least one characteristic of the hand 214 based on information from the sensor 204. In the example, the sensor 204 detects the hand 214 and the dispenser 200 determines that the hand 214 has been positioned within the housing 202 within range of spray from the nozzles 206. In some embodiments, the dispenser 200 may determine the length, width, and depth of the palm of the hand based on information from the sensor 204.

The dispenser 200 causes the liquid barrier precursor material 217 to be sprayed through the nozzles 206 onto the hand 214 within the interior space 208. The dispenser 200 may spray the palm, the back of the hand, the sides of the hand, and/or portions of the wrist and arm of the person. The liquid barrier precursor material 217 cures, e.g., dries, to form the hand barrier 219. Suitably, the liquid barrier precursor material 217 may dry within 2 seconds after being applied onto the hand 214 within the interior space 208. The barrier 219 may be completely dry after the hand 214 is removed from the housing 202. The barrier 219 is at least partially transparent and is less than 1 millimeter thick. Accordingly, the barrier 219 does not affect the wearer's use of the hand. For example, the wearer is able to operate touch screens or handheld electronic devices with the hand 214 while wearing the barrier 219.

The liquid barrier solution 217 is made of natural ingredients and is biodegradable such that the barrier can be easily disposed of after use. In addition, the liquid barrier solution 217 and, thus, the hand barrier 219 are free of latex and other materials that may irritate a person's skin. As used herein, the term "skin irritant" refers to materials that remove the skin's moisture or oils, are common allergens, or otherwise irritate the skin. Examples of skin irritants include soap, latex, and detergents.

The liquid barrier solution may be mixed in the reservoir connected to the dispenser 200. The liquid barrier solution in the reservoir may be mixed continuously or intermittently. In other embodiments, the liquid barrier solution is mixed at a manufacturing station and the reservoir for the dispenser 200 is provided with premixed solution. In some embodiments, the reservoir 212 may include a stirrer configured to keep the liquid barrier precursor material 217 agitated and maintained in a desired state. In some embodiments, the dispenser 200 and/or the reservoir 212 includes an indicator 216 configured to indicate when the amount of liquid barrier precursor material 217 in the reservoir 212 is below a threshold level. In the example, the reservoir 212 includes the indicator 216. The indicator 216 may include a light and/or speaker.

The dispenser 200 may record information regarding operation. For example, the dispenser 200 may record the amount of liquid barrier precursor material 217 used, the amount of liquid barrier precursor material 217 in the reservoir 212, how many hands are scanned on a daily basis, the average time required to scan and/or dispense a barrier onto a hand, coverage of the barrier on the hand, and any other suitable data. The dispenser 200 may utilize the sensor 204 and/or one or more additional sensors to collect data. The dispenser 200 may provide information to a remote computing device, a server, or a user via a display. The collected data may be used to generate reports such as reports for government agencies or other authorities.

Figure 6:
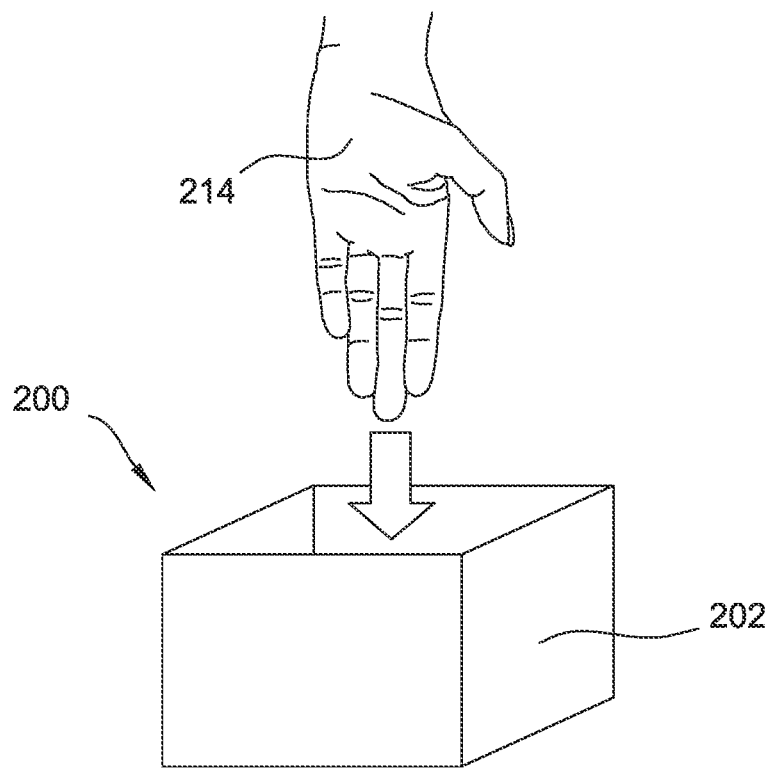
FIG. 6 is a schematic view of an embodiment of a housing for the dispenser of FIG. 5, the housing configured to receive a hand from a first direction.
Figure 7:
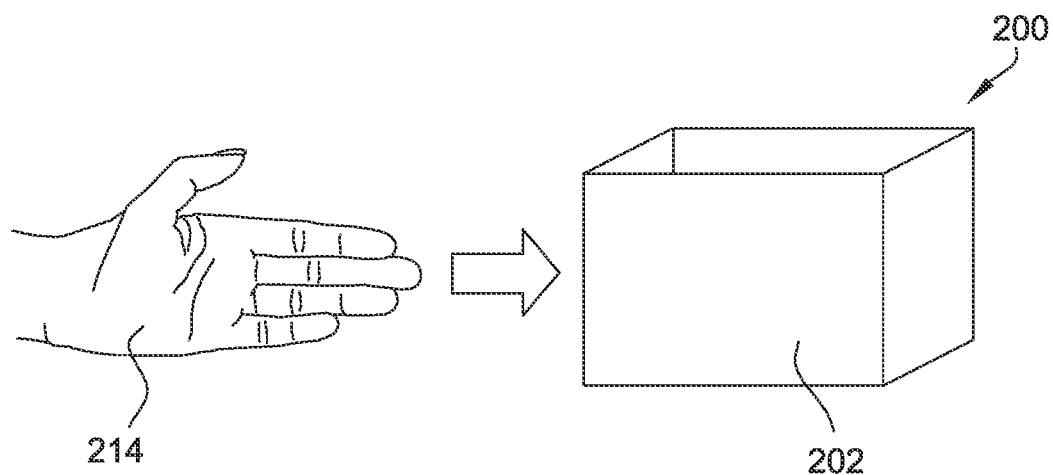
FIG. 7 is a schematic view of another embodiment of a housing for the dispenser of FIG. 5, the housing configured to receive a hand from a second direction.
Figure 8:
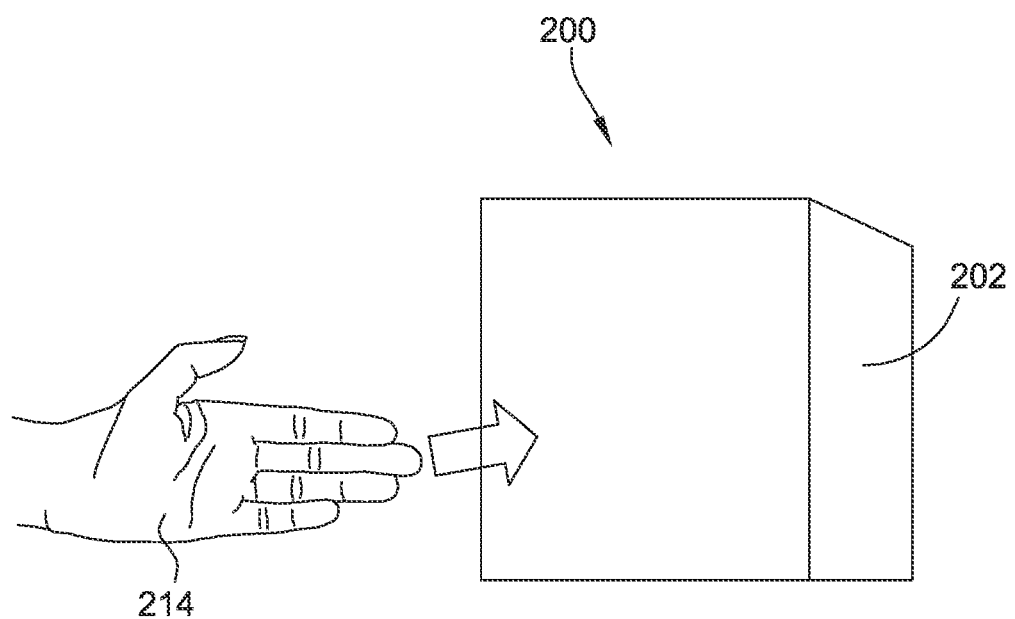
FIG. 8 is a schematic view of yet another embodiment of a housing for the dispenser of FIG. 5, the housing configured to receive a hand from a third direction.

FIGS. 6-8 show a hand 214 being positioned into the interior space 208 of the housing 202 in different directions. The housing 202 may include one or more openings configured to receive the hand 214 in the different directions. Suitably, the housing 202 may include doors or the walls may be adjustable to receive the hand from the different directions. The different orientations or configurations of the housing 202 facilitate the dispenser 200 being used in different locations and for different applications.

In some embodiments, the liquid barrier dispenser may be configured as a one-time use or portable device for personal use by an individual. For example, the dispenser may comprise a bottle configured to contain a liquid barrier precursor material and a squirt tip dispenser connected to the bottle. The liquid may be dispensed by pumping the top and/or squeezing the bottle. The liquid may thus be applied to the individual's hands. Accordingly, the dispenser may be portable to allow a person to carry the dispenser around for personal use whenever a hand barrier is useful.

Suitably, the hand barrier may dissolve when washed off and/or the hand barrier may be simply peeled off of the hands.

The hand barrier provided by the described systems is a covering that wraps the entire hand to protect the individual's skin from attracting microorganisms such as germs, bacteria, or other virus causing pathogens that are often transferred through touch.

The barrier precursor solution may comprise additives, an oil, an adhesive, a solvent, and any other suitable ingredients. In one embodiment, the barrier precursor solution comprises:
  Capric Triglyceride
  Squalane (e.g., obtained from animal components such as shark skin or from plants).
  Glycerly Monosterate
  An oil-in-water emulsifier (e.g., Arlacel™ 1689 provided by Croda Personal Care)
  Lavender Oil
  Almond Oil.
  Animal skin (e.g., shark skin).
  Tocopheral-d-alpha 50% (Vitamin E).
  Food Coloring.
  PVA Glue
  Corn Starch.
  Water/Ethanol The described ingredients of the barrier precursor solution facilitate the solution being applied to and adhering to the hand. In addition, the solution is able to cure within 2 seconds after being applied to the hand. Also, the solution is free of irritants or non-biodegradable materials. Moreover, the solution provides an anti-microbial barrier that conforms to a shape of the hand and does not hinder use of the hands. For example, the hand barrier may allow the wearer to operate a touchscreen or handheld device with their hands while wearing the barrier. In addition, the barrier is simple to remove or wash off after use. In other embodiments, the barrier precursor solution may include additional or different ingredients. For example, in some embodiments, the barrier precursor solution includes zinc oxide.

Figure 9:
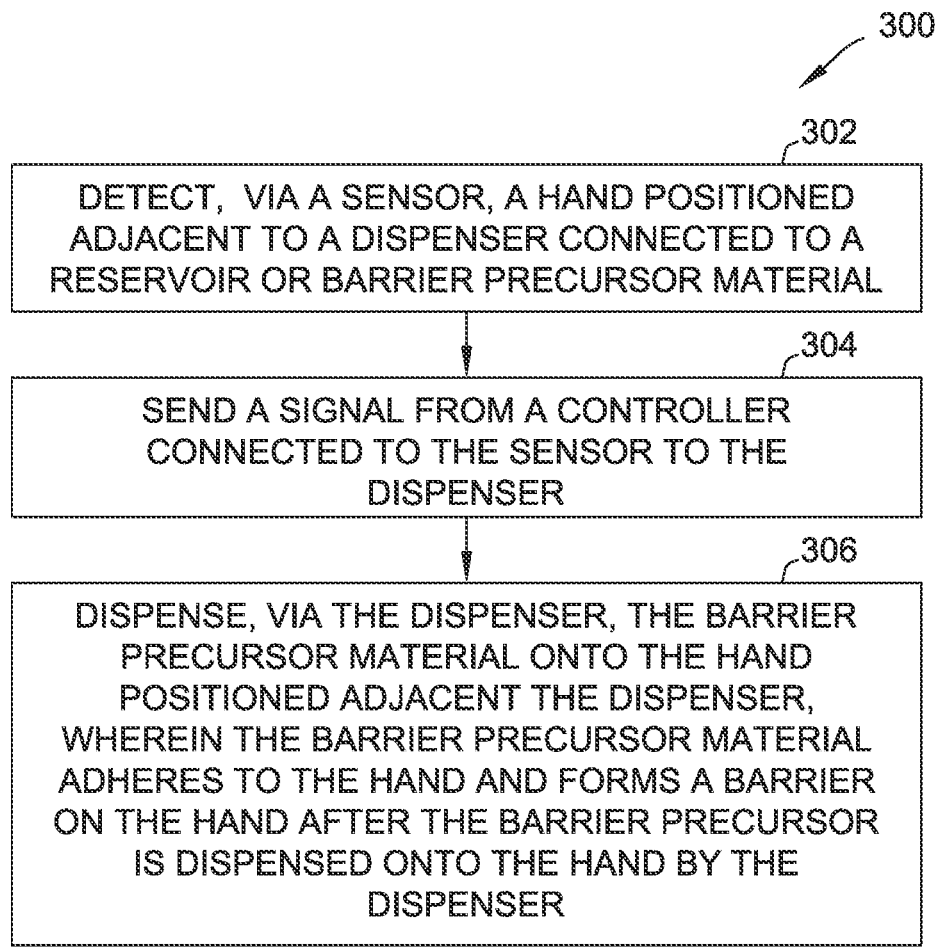
FIG. 9 is a flow chart of a method of applying an antimicrobial barrier onto a hand.

FIG. 9 is a flow chart of a method 300 of protecting a hand with a hand barrier. The method 300 includes detecting 302 a hand positioned adjacent a dispenser connected to a reservoir of barrier precursor material. For example, the dispenser may be mounted to a housing and a sensor may detect when a hand is positioned within an interior space of the housing and within range of the dispenser. In some embodiments, the method 300 includes opening a door of the housing to allow the hand to be positioned within the interior space.

The method 300 further includes sending 304 a signal from a controller connected to the sensor to the dispenser. For example, the dispenser may receive at least one characteristic of the hand based on information from the sensor. For example, the controller may determine a size and shape of the hand based on information from the sensor and send information relating to the size and shape of the hand to the dispenser. In further embodiments, the sensor detects a presence or proximity of the hand and the controller sends an activation signal to cause the dispenser to dispense a barrier based on the detected presence.

The method 300 also includes dispensing 306 the barrier precursor material onto the hand positioned adjacent the dispenser. The barrier precursor material adheres to the hand and forms a barrier when the barrier precursor is dispensed onto the hand by the dispenser. In some embodiments, the method 300 may include curing or drying the barrier precursor material to form the barrier within the interior space of the housing. The barrier precursor material may be cured using a heat source, UV rays, a moving fluid source, and/or any other suitable drying element. For example, in some embodiments, the hand is positioned in a dryer, a heater, a form, and/or forced airflow to promote curing of the barrier precursor material.

Figure 10:
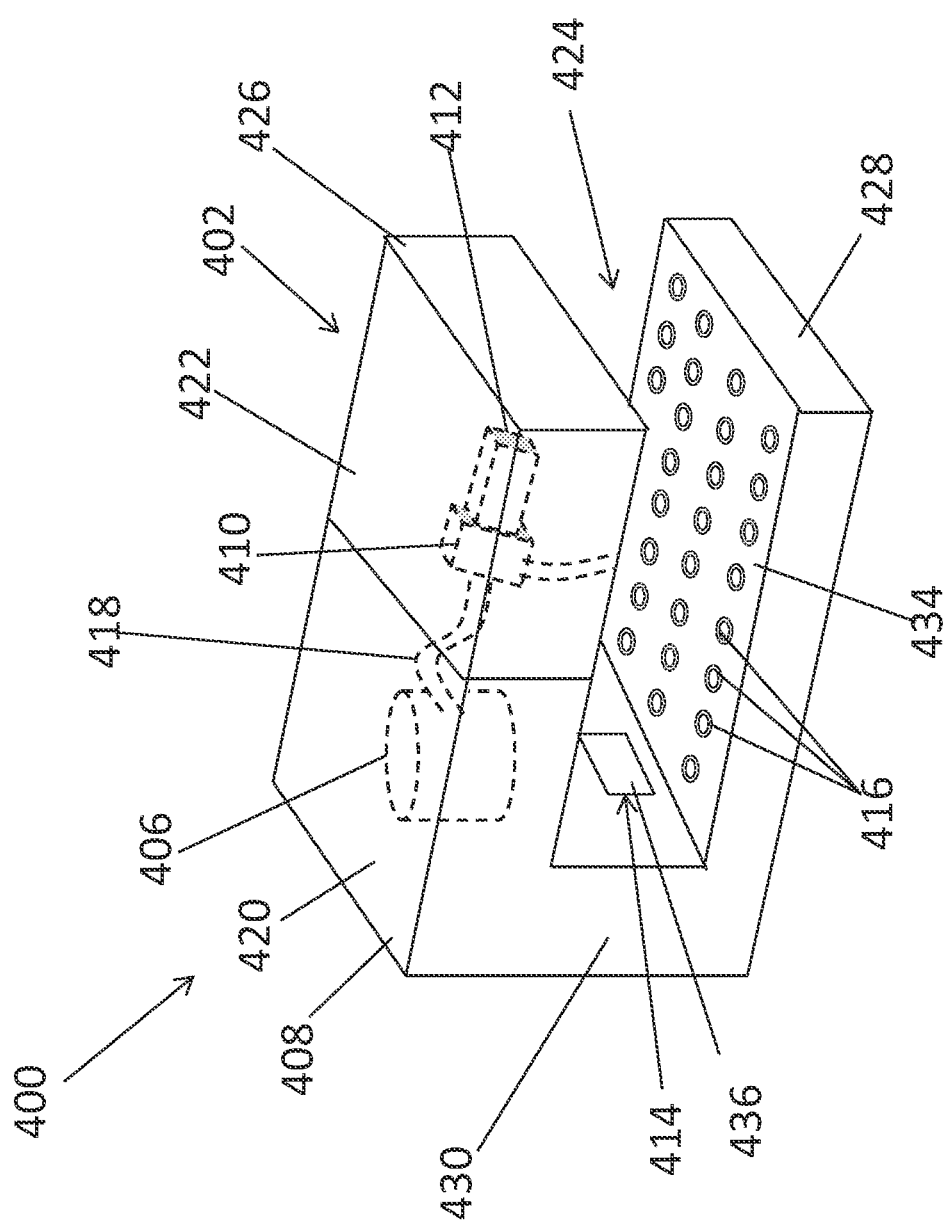
FIG. 10 is a perspective view of a system for applying a hand barrier.
Figure 11:
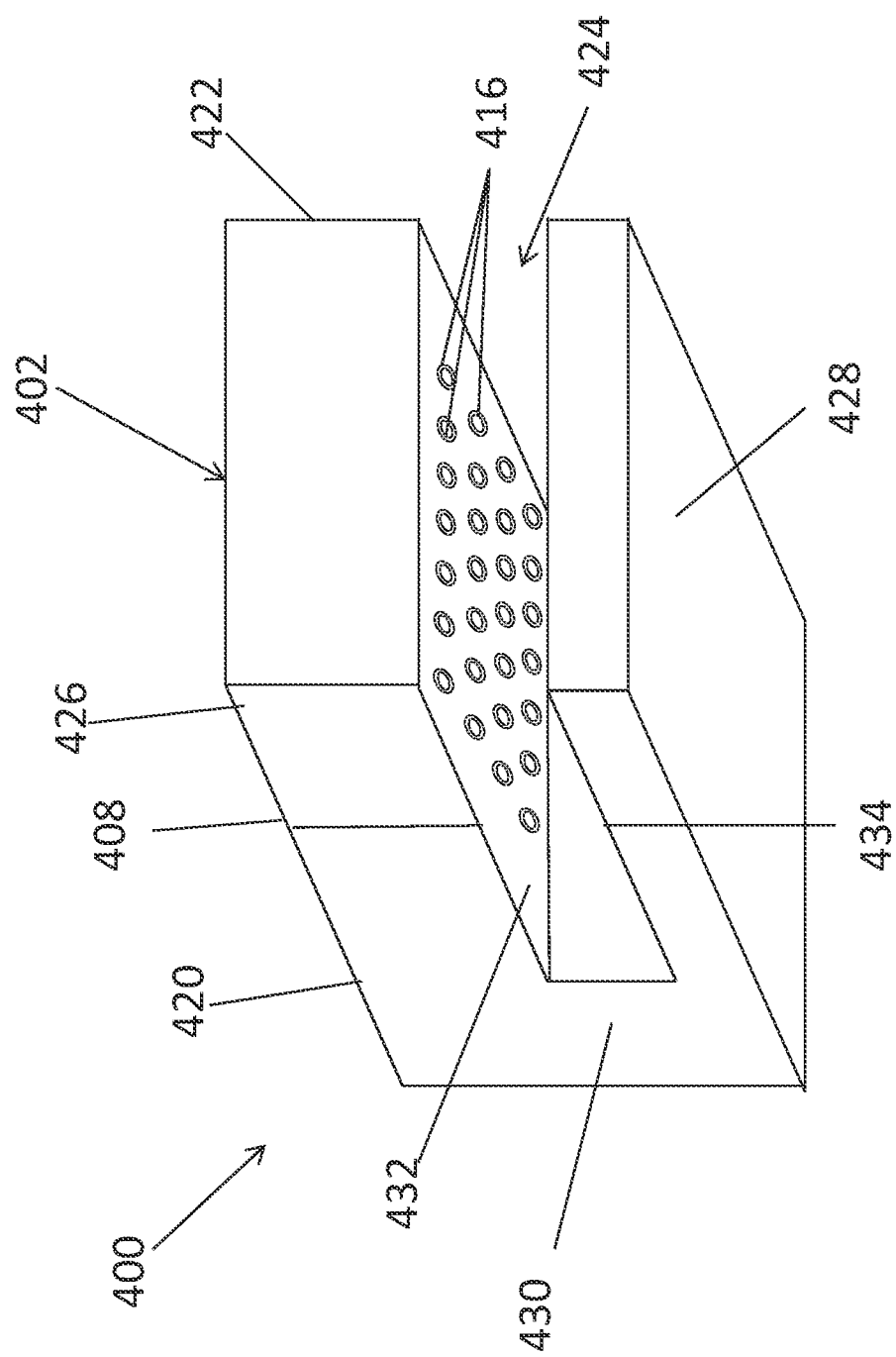
FIG. 11 is another perspective view of the system shown in FIG. 10.
Figure 12:
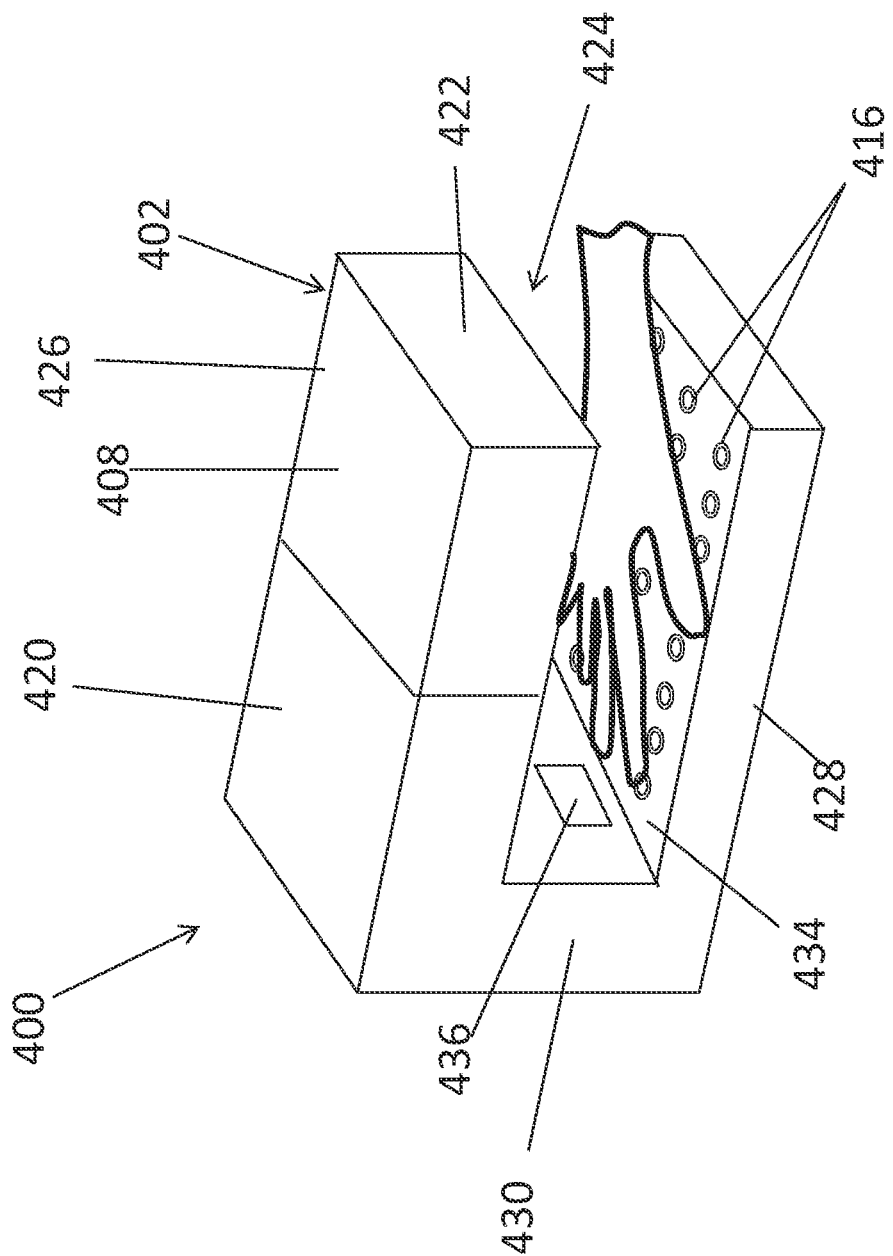
FIG. 12 is a perspective view of the system shown in FIG. 10 with a hand position for application of the hand barrier.
Figure 13:
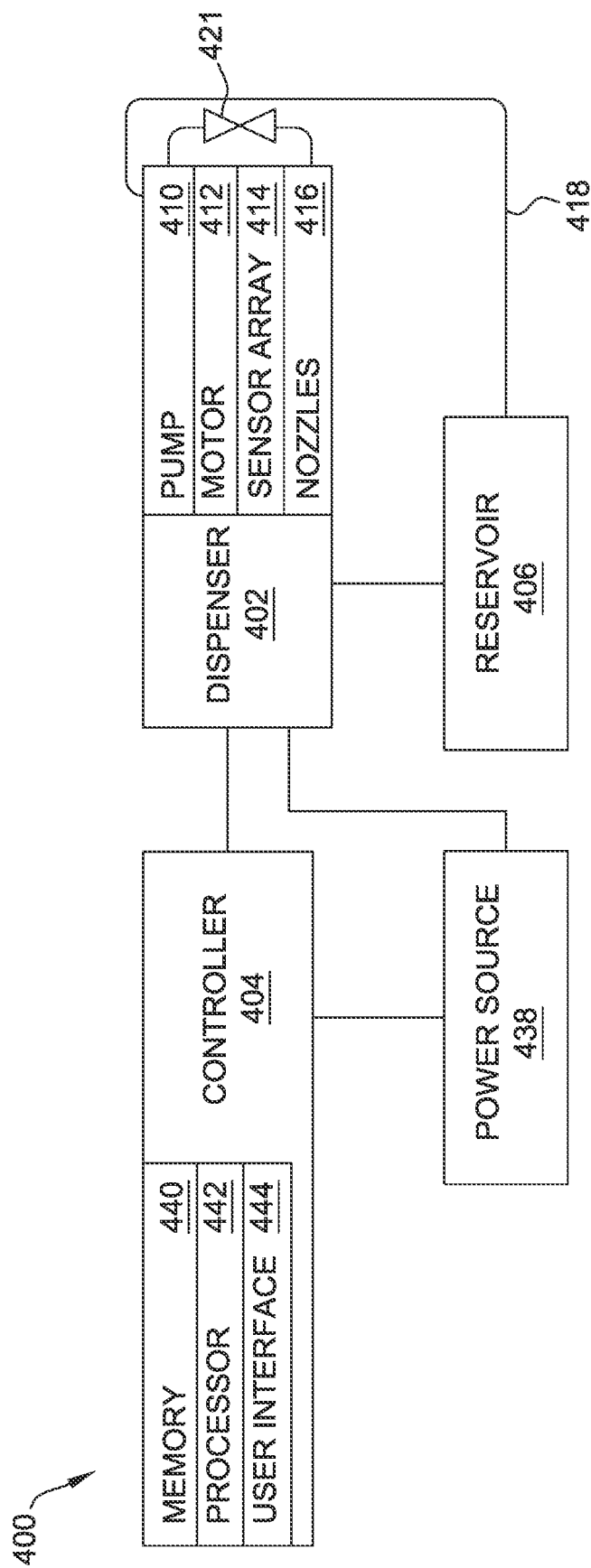
FIG. 13 is a block diagram of the system shown in FIG. 10.

FIGS. 10 and 11 are perspective views of an embodiment of a system 400 for applying a hand barrier. FIG. 12 shows a hand positioned to receive a hand barrier from the system 400. FIG. 13 is a block diagram of the system 400. The system 400 includes a dispenser 402, a controller 404, and a reservoir 406 of a barrier precursor material. The dispenser 402 includes a housing 408, a pump 410, a motor 412, a sensor array 414, and at least one nozzle 416. In other embodiments, the system 400 may include any components that enable the system to operate as described herein.

The controller 404, the pump 410, the motor 412, the sensor array 414, and the at least one nozzle 416 are mounted to or housed within the housing 408. For example, the housing 408 includes a first compartment 420 containing the reservoir 406 and a second compartment 422 configured to house the motor 412, the controller 404, and the pump 410. The reservoir 406 and/or the first compartment 420 is sealed to prevent leakage of the solution and prevent the barrier precursor solution from being contaminated. In some embodiments, the reservoir 406 includes temperature, humidity, and/or any suitable environmental controls to provide a desired environment for the barrier precursor material. For example, in some embodiments, the system 400 may include a heat exchanger configured to maintain the barrier precursor material at a temperature selected to maintain the barrier precursor material in a desired state. In some embodiments, the reservoir 406 may include a mixing device to stir or mix the material and maintain a desired mixture and consistency of the material.

In addition, the housing 408 defines a receiving cavity 424 configured to receive a hand for the dispenser 402 to dispense a barrier onto the hand. In some embodiments, the receiving cavity 424 is sized to receive two hands. In the example, the housing 408 includes an upper portion 426, a base 428, and a support 430 extending between the upper portion 426 and the base 428 to support the upper portion 426 above the base 428. The upper portion 426, the support 430, and the base 428 collectively define the receiving cavity 424 and form a U-shape such that the hand is positioned between the upper portion 426 and the base 428 in the receiving cavity 424. In the example, the upper portion 426 includes at least a portion of the first compartment 420 and the second compartment 422.

The housing 408 provides security, modularity, and ease of maintenance. For example, the housing 408 encloses the components to protect the components from the environment and prevent tampering. In some embodiments, the housing 408 includes a key lock mechanism to prevent access by unauthorized persons. The housing 408 also maintains the safety of end users by providing a barrier between them and moving parts within the housing 408 such as the motor 412 and the pump 410. In addition, the housing 408 is modular and is compatible with different components such as different controllers 404, motors 412, pumps 410, and nozzles 416. In addition, the housing 408 may receive curing components such as fans, heaters, and/or lights. For example, the curing components may be mounted to the upper portion 426, the base 428, and/or the support 430 adjacent the hand receiving cavity 424.

In the example, the at least one nozzle 416 is configured to receive the solution from the reservoir 406 for spraying. For example, one or more fluid lines 418 extend from the reservoir 406 to the at least one nozzle 416. The pump 410 is coupled along the one or more fluid lines 418 and is configured to draw fluid through the fluid lines and cause the fluid to flow from the reservoir 406 to the at least one nozzle 416. In the example, at least one valve 421 is connected to the fluid lines 418 to regulate fluid flow through the fluid lines 418.

The at least one nozzle 416 is mounted to the housing 408 and positioned to spray the solution onto a hand positioned within the receiving cavity 424. For example, the at least one nozzle 416 includes a first set of nozzles 416 mounted to an upper wall 432 of the base 428 and a second set of nozzles 416 mounted to a lower wall 434 of the upper portion 426. The nozzles 416 on the upper wall 432 are oriented opposite the nozzles 416 on the lower wall 434 such that the nozzles 416 simultaneously spray solution onto both sides of a hand. Each nozzle 416 has a nozzle tip that may be adjustable and/or replaceable to provide a different spray pattern. For example, the nozzles 416 have tips that provide fan, full cone, mist, and/or any other suitable spray type.

The sensor array 414 includes at least one sensor 436 configured to detect at least one characteristic of the hand. For example, the sensor 436 may include a proximity sensor that detects the hand 120 when the hand 120 is adjacent the housing 408 and/or when the hand 120 is within the receiving cavity 424. In some embodiments, the sensor array 414 includes a scanner that is configured to generate an image of the hand 120. The image of the hand 120 depicts the shape and size of the hand 120. In embodiments, the sensor array 414 may include one or more of the following sensors: an infrared sensor, a temperature sensor, a moisture sensor, and any other suitable sensor.

The controller 404 is connected to the sensor array 414 and is configured to receive information from the sensor array 414. The controller 404 is configured to determine characteristics of the hand 120 based on the information from the sensor array 414. For example, the controller 404 may determine the size and shape of the hand 120 from an image received from the scanner and determine a suitable size and shape of the hand barrier based on the image of the hand 120. In some embodiments, the controller 404 controls components of the system 400 such as the dispenser 402 based on information from the sensor array 414. For example, the controller 404 controls operation of the motor 412 and the pump 410 to supply fluid to the nozzles 416 to spray onto the hand 120.

The controller 404 and/or the dispenser 402 are connected to a power source 438 that is configured to provide electrical power to the system 100. In the example, the power source 438 includes a battery that is housed within the housing 408. The controller 404 may be configured to monitor the power levels of the power source 438 and provide an indication based on the power levels. For example, the controller 404 may automatically send an alert to a remote computer when the power level of the power source 438 is below a threshold. In some embodiments, the system 100 is connected at least temporarily to an external power source. For example, the system 400 may include a cord that connects to an external power source to recharge the battery. In some embodiments, the battery is omitted and the system 400 receives power from the power source 438 which is located exterior of the housing 408.

The controller 404 includes a memory 440, a processor 442, and a user interface 444 including an input device and a display. The controller 404 may control operation of components of the system 400, such as the dispenser 402, to dispense the protective barrier onto the hand 120. The controller 404 may operate in accordance with instructions stored on the memory 440 or an external memory to perform any steps of the methods described herein.

During operation, individuals can place there hand into the receiving cavity 424. The sensor array 414 detects at least one characteristic of the hand 120 and the controller 404 causes the motor 412 and the pump 410 to operate to draw the solution from the reservoir 406 to the nozzles 416. The barrier is then applied to and adheres to the hand. The barrier cures on the hand after application. Suitably, the barrier cures within 2 seconds of application. The user interface 444 may provide indications to the user indicating when the dispenser 402 is ready to receive a hand, when the solution is being sprayed, and/or when the hand barrier has been successfully applied to the hand and the hand may be removed.

Figure 14:
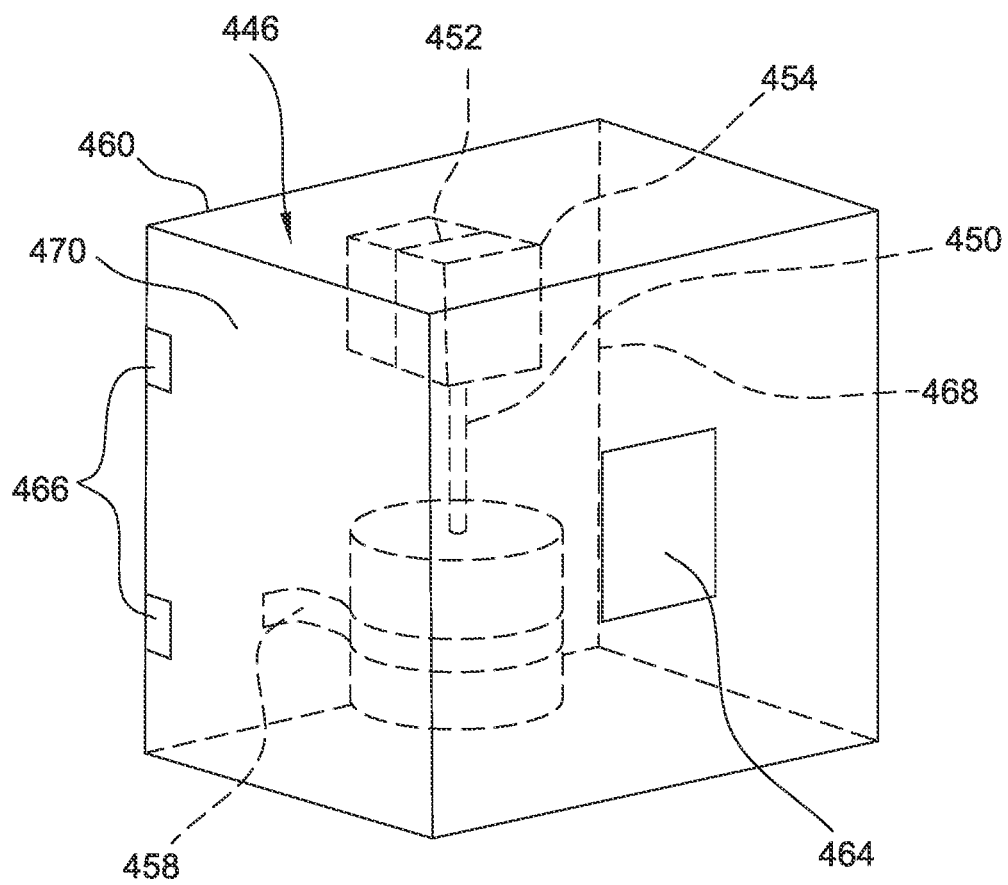
FIG. 14 is a perspective view of a mixing device for use with the system shown in FIG. 10.
Figure 15:
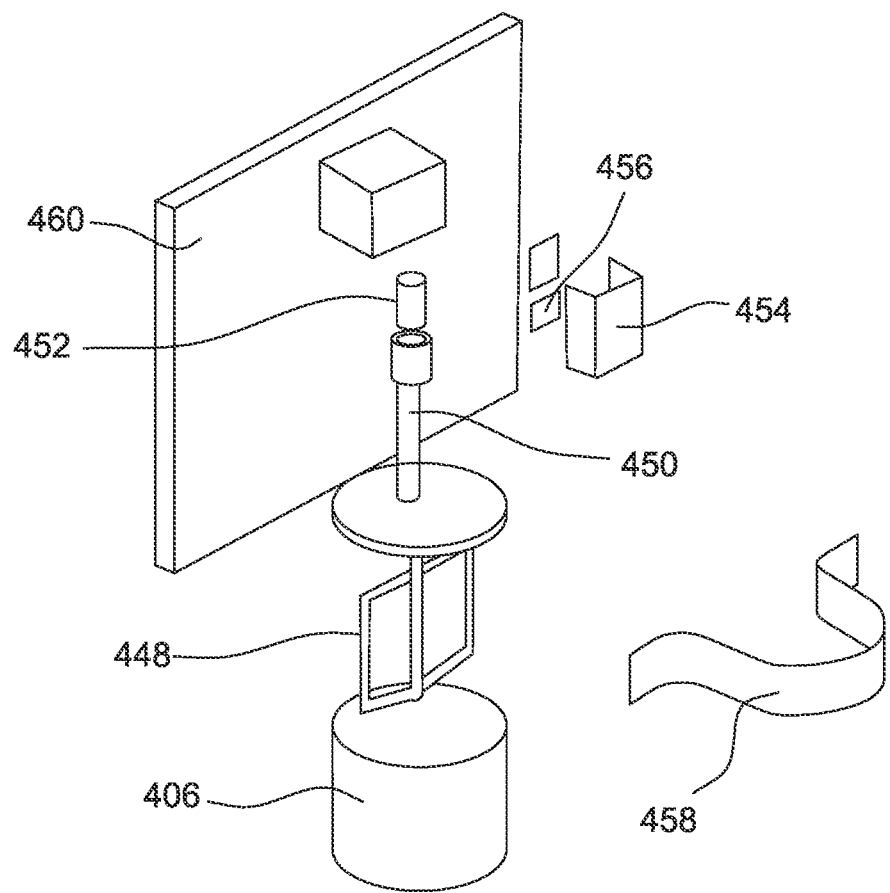
FIG. 15 is a partially exploded view of the mixing device shown in FIG. 14.

FIGS. 14 and 15 show a mixing device 446 for use with the system 400 (shown in FIG. 10). For example, as shown in FIG. 14, the mixing device 446 is positioned at least partly within the reservoir 406 and is configured to mix or agitate the solution within the reservoir 406. The mixing device 446 includes an impeller 448, a rotatable shaft 450, a motor 452, a motor housing 454, and a motor controller 456. The mixing device 446 and the reservoir 406 are secured to a wall 460 of the first compartment 420 by a support structure 458. The support structure 458 includes, for example, a clamp. The support structure 458 extends around the reservoir 406 and secures to the wall 460. In addition, the motor housing 454 secures to the wall 460.

The impeller 448 is connected to the rotatable shaft 450 which is driven by the motor 452. The motor 452 causes rotation of the rotatable shaft 450 which drives the impeller 448 to rotate within the reservoir 406 and mix the solution within the reservoir 406.

Referring to FIG. 14, in the illustrated embodiment, the first compartment 420 includes a touchscreen 464, hinges 466, and a lock mechanism 468. At least a portion of the first compartment 420 is movable to provide access to the mixing device 446 within the first compartment 420. For example, the first compartment 420 includes a cover 470 that is pivotably connected to the wall 460 by the hinges such that the cover 470 is positionable between an open position and a close position. The touchscreen 464 and/or the lock mechanism 468 are used to restrict/grant access to position the cover 470 between the open and close positions.

Figure 16:
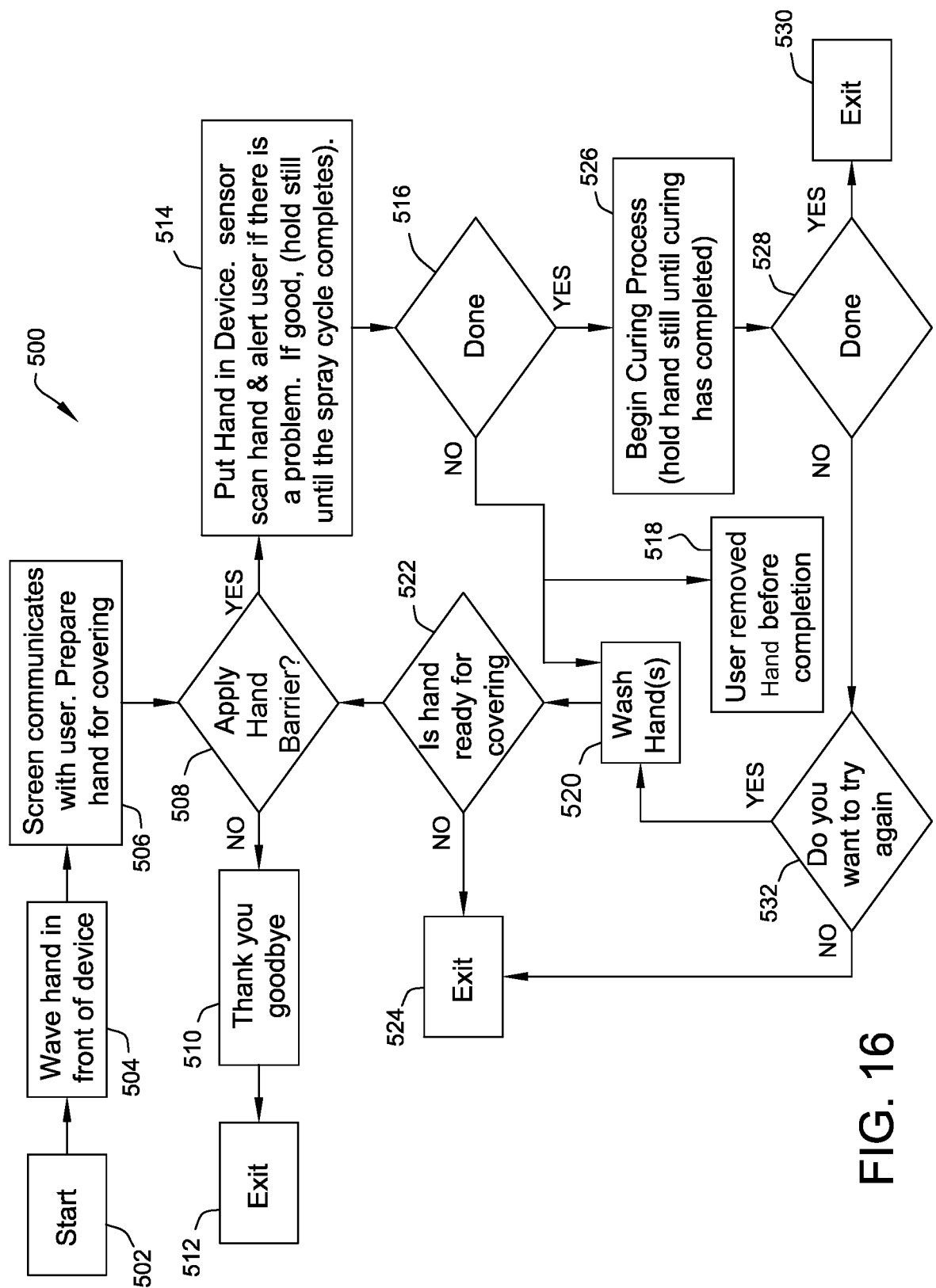
FIG. 16 is a flow chart of a method of applying a barrier onto a hand, using a system such as the system shown in FIG. 10.
Figure 17:
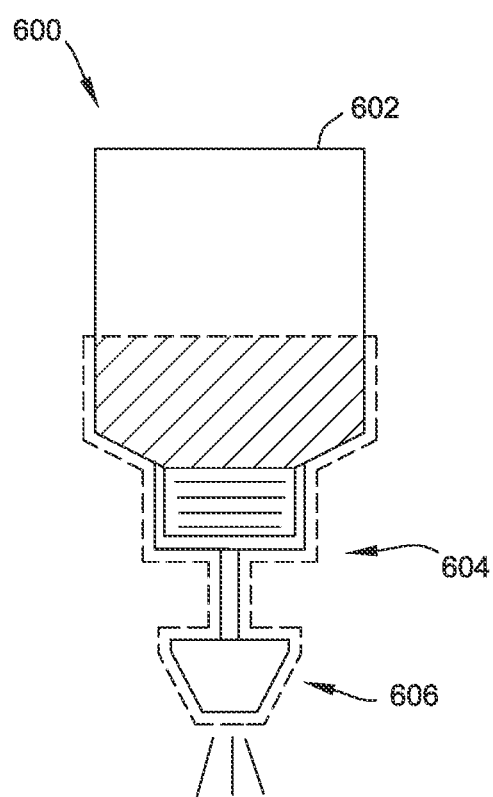
FIG. 17 is a schematic view of an example of a dispenser for an antibacterial solution.

FIG. 16 is a flow diagram of an embodiment of a method 500 of protecting a hand with a hand barrier using a system such as the system 100, the dispenser 200, or the system 400. Referring to FIGS. 9-12, the method 500 includes starting 502 when a user approaches the dispenser 402. The user activates 504 the dispenser 402 by, for example, approaching the dispenser 402 and/or waving a hand in front of the dispenser 402. The user interface 444 communicates 506 with the user by, for example, providing a message to the user to prepare a hand(s) for covering. The message may be provided as a visual message on the display, an auditory signal, a visual indication, and/or in any other suitable manner.

The dispenser 402 determines 508 if the protected covering will be applied. For example, the system 400 determines to apply the protective coating when the user positions the hand within the receiving cavity 424 or otherwise positions the hand relative to the dispenser 402 to receive the protective coating. In some embodiments, the user may be required to select an option on the user interface to establish authorization for use, or provide payment or proof of payment before the system 400 will apply the protected coating. If the system 400 determines not to apply protective barrier, the user interface 444 provides a goodbye message 510 to the user and exits 512 the protocol.

The method 500 includes receiving 514 a hand in the dispenser 402 if the dispenser 402 determines that the protective covering will be applied to the hand. The sensor array 414 detects and scans the hand and the controller 404 determines if the hand is ready for application. The user interface 444 provides an alert to the user if there is an issue with applying the protective barrier to the hand. If the controller does not detect an issue, the dispenser 402 applies the protective barrier to the hand. The user interface 444 provides an indication to maintain the hand still within the receiving cavity 424 during the application process.

After application, the controller 404 determines if the protective coating was correctly applied and the application process was completed 516 based on information from the sensor array 414. If the application process was not completed, the controller 404 determines if the hand was removed 518 from the receiving cavity 424 before completion of the application process. If the hand was removed prematurely, the user interface 444 may prompt the user to reinsert the hand to complete or start a new application process. If the controller 404 determines that the application process was not completed due to an issue with the hands, the controller 404 provides feedback to the user, via the user interface 444, to, for example, wash the hand(s) 520. The user interface 444 provides an option for the user to select if the hand is ready for covering 522 after the user washes the hand(s). In some embodiments, the system 400 may include a hand washing station for the user to wash the hand(s) before receiving the protective barrier and/or after the user is finished with the protective barrier. If the user selects that the hand is ready for the protective barrier, the method 500 returns to determining 508 to apply the protective coating. The system 400 exits 524 the protocol if the hand is not ready for the protective barrier.

The method 500 includes curing 526 the precursor solution after application to form the protective barrier. The user interface 444 provides a message to the user to maintain the hand still until the curing process has completed and indicates to the user when the curing process is complete and the user can remove the hand. The controller 404 determines 528 if the curing process was successfully completed. If the curing process was completed, the controller 404 exits 530 the protocol. In some embodiments, the user interface 444 provides an indication to the user to prepare a second hand for application if only one hand was covered during the initial iteration. Then, the method 500 starts over to apply the protective barrier to the subsequent hand. If the curing process was not completed, the user interface 444 allows the user to select 532 if they want to try again. If the user selects not to attempt to apply the protective barrier again, the controller 404 exits 524 the protocol. If the user selects to attempt to apply the protective coating again, the method 500 moves to prompting the user to wash the hand(s) 520.

EXAMPLE

As shown in FIG. 16, an example dispenser 600 was assembled including a tank or reservoir 602, a pump 604, and a nozzle 606. For example, the dispenser 600 could be configured as a personal use or portable dispenser 600 for a user to carry around. In some embodiments, the dispenser 600 is mounted to a support for public use. Suitably, the dispenser 600 does not require a battery source because the pump 604 is manual.

A mathematical model was designed to determine how much pump head would be needed to dispense the solution from the dispenser 600. A control volume of barrier precursor solution was deposited into the reservoir 602. The model assumes a slightly lower pressure in the reservoir 602 than atmospheric pressure. An electric actuator (not shown) was used to press the manual pump 604 to spray the solution. The control volume is surrounded by a dashed line.

Bernoulli's equation (Eq. 1) was used to determine the necessary pump head for various nozzle types. Bernoulli's equation deals with inviscid flow (viscosity of the fluid is equal to zero). While the solution does have a viscosity greater than zero, the following equation was used to provide approximate results by neglecting viscosity:

E-1: Bernoulli's Equation $$\left(\frac{P_t}{\gamma} + \frac{V_t^2}{2g} + z_t\right) = \left(\frac{P_n}{\gamma} + \frac{V_n^2}{2g} + z_n\right) + h_f + h_m - h_p \qquad \text{Eq. (1)}$$

where $P_t$ is pressure at the top of the reservoir in pascals (Pa), $P_n$ is pressure at the nozzle outlet in Pa, $V_t$ is velocity of fluid at the top of the storage tank in meters per second (m/s), $V_n$ is velocity of fluid at the nozzle outlet in m/s, $z_t$ is the height of solution in the reservoir above a fixed datum line in meters (m), y is specific gravity of the solution in kilograms per cubic meter (kg/m$^3$), g is acceleration due to gravity in square meters per second (m$^2$/s), hf is frictional losses in m, hm is minor losses in m, hp is pump head in m.

Bernoulli's equation can be simplified by ignoring change in elevation, assuming negligible frictional had loss, and assuming a negligible velocity in the tank. The simplified equation is:

E-2: Simplified Bernoulli's Equation $$h_p = \frac{V_n^2}{2g} + h_m - \frac{P_n - P_t}{\gamma} \qquad \text{Eq. (2)}$$

The equation can be further defined by using Equations 3 and 4 below to define the minor losses and nozzle velocity. The volumetric flow rate based on the application process having a duration of ½ second and dividing the flow rate from the volume needed per application (using the thickness $t_1$, $t_2$, $t_3$ and the average area of 43 m$^2$).

$$h_m = \sum K * \frac{V_n^2}{2g} \qquad \text{Eq. (3)}$$

$$V_n = \frac{Q}{A_n} \qquad \text{Eq. (4)}$$

Figure 18:
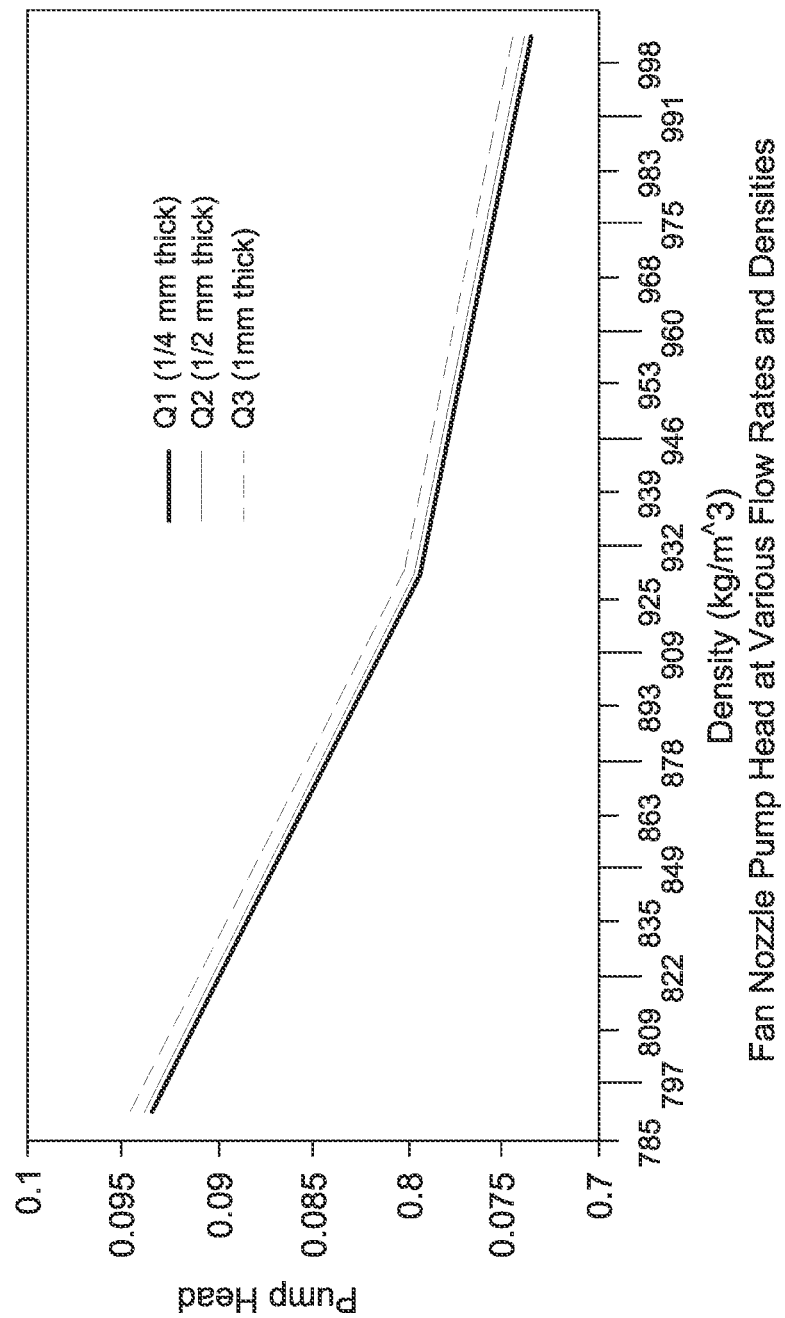
FIG. 18 is a line graph of pump head versus density for the dispenser shown in FIG. 17 with a fan type nozzle.
Figure 19:
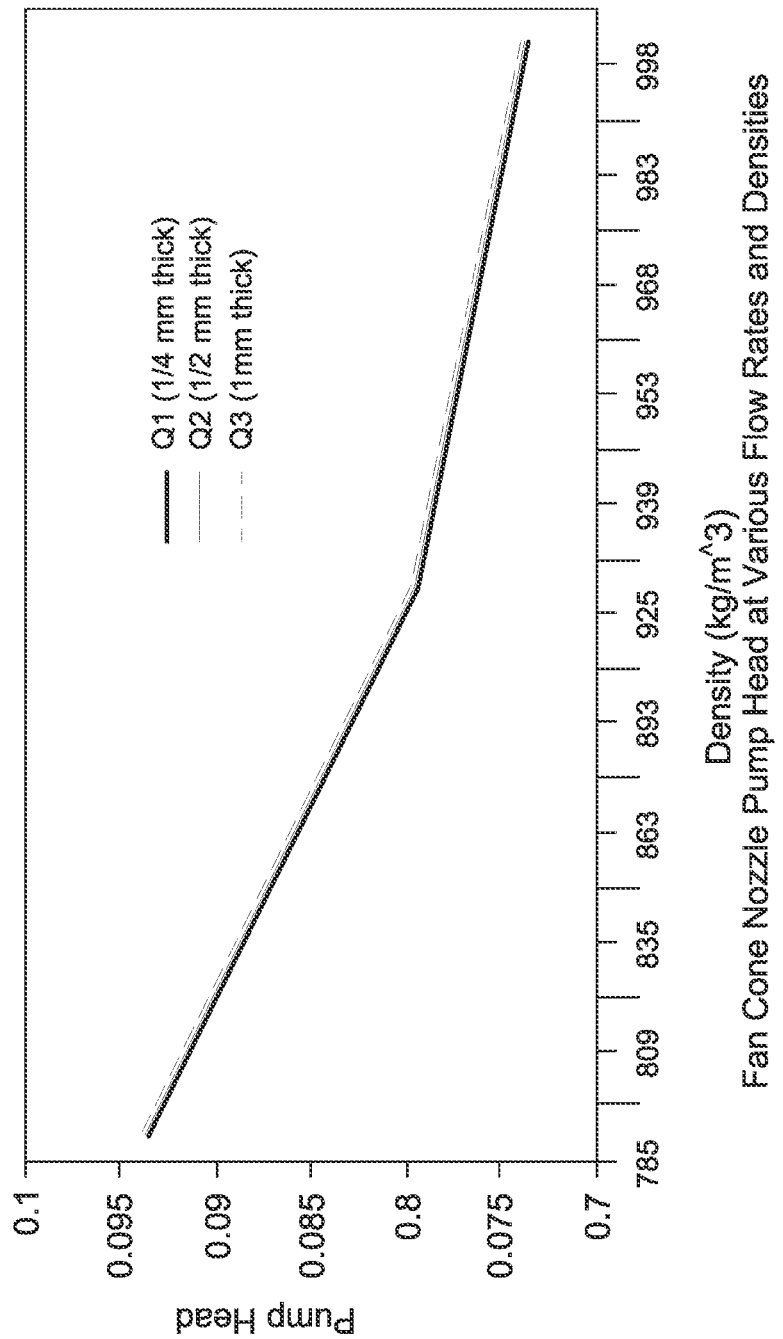
FIG. 19 is a line graph of pump head versus density for the dispenser shown in FIG. 17 with a full cone type nozzle.

The pump head calculations were iterated over the range of densities for a solution mixed with isopropyl alcohol or water at various ratios (100% Isopropyl through 100% solution, 100% water through 100% solution). The iterations were done for three different nozzle types fan, full cone, and mist. These nozzles provided different K values and free areas. The nozzle values were provided by a nozzle manufacturer. FIG. 18 shows the pump head versus density for the dispenser 600 with a fan type nozzle. FIG. 19 shows the pump head versus density for the dispenser 600 with a full cone type nozzle.

The dispenser 600 was configured to contain and dispense a premixed solution. If continued mixing is required, a mixing device such as an anchor impellor and a motor to drive the impellor could be incorporated into the dispenser 600. In the example, the reservoir 602 contains enough solution to cover between 10-15 hands. The following mathematical equation was used to determine the amount of solution to place in the reservoir to hold enough solution that would cover 10-15 hands.

$$V=mp \qquad \text{Eq. (5)}$$

where V is a volume of fluid, m is a total mass, and p is the solution's density. The mass was calculated by dividing the object's weight by the acceleration of gravity (9.8 meters/seconds).

Also, the height and inner diameter of the cylindrical reservoir were determined to contain the desired volume of solution. In the example, the reservoir 602 contains a square batch in which the liquid height is equal to the reservoir diameter. Accordingly, the square batch is calculated using the reservoir diameter with the following equation:

$$T_{eq} = \left(\frac{4}{\pi} * V\right)^{1/3} \qquad \text{Eq. (6)}$$

where $T_{eq}$ is the reservoir diameter/liquid height.

In embodiments with an impeller, the impeller diameter can be determined to be 90% the size of the inner diameter of the reservoir. The impeller would be driven by a motor to mix the solution within the reservoir 602. The Reynolds number for the impeller is used to determine the size of the motor to drive the impeller, using the following equation:

$$N_{R_e} = \frac{10.7 D^2 N_p}{u} \qquad \text{Eq. (7)}$$

where 10.7 is a factor used for unit conversions, D is diameter, Np is the power number. For Reynolds number <10, laminar flow exists. With N, the shaft's rotational speed at 75 RPM, the impeller Reynolds number is calculated as 0.208 in the example.

For laminar flow conditions, the power number Np is determined using the following equation:

$$N_p \propto \left(\frac{s}{T}\right)^{-0.5} \qquad \text{Eq. (8)}$$

where e is the clearance between the wall and the impeller blade, and T is the reservoir diameter.

Figure 20:
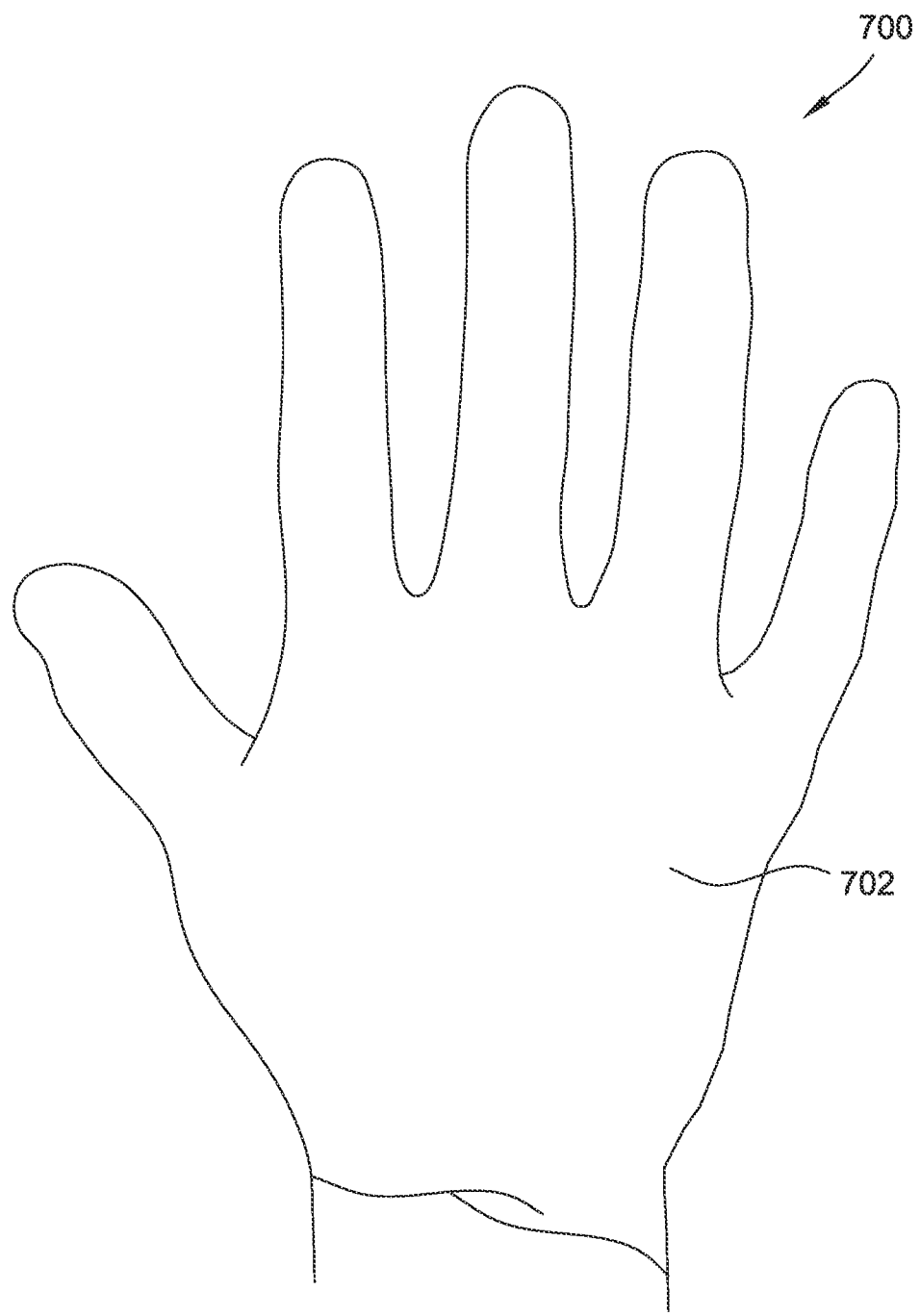
FIG. 20 is an illustration of a hand protected by a hand barrier.

FIG. 20 is an illustration of a hand 700 protected by a hand barrier 702. The hand barrier 702 is applied to the hand 700 using the systems and methods described herein. The hand barrier 702 entirely covers the hand 700. The hand barrier 702 is applied as a liquid or semiliquid solution that cures to form the hand barrier 702. The hand barrier 702 includes a thin, flexible layer that conforms to the shape of the hand 700. In some embodiments, the hand barrier 702 has a uniform thickness throughout. In other embodiments, the hand barrier 702 is provided with an increased thickness in selected areas to provide an increased protection or strength for portions of the hand 700. The hand barrier 702 may be clear, blue, red, green, yellow, black, white, or any other suitable color. The color of the hand barrier 702 may provide a visual indication that the hand 700 is protected by the hand barrier 702.

Some embodiments of a hand barrier system include a biodegradable antimicrobial solution sprayed onto a hand to provide a hand barrier that reduces microorganisms that are spread through touch. The hand barrier prevents a wearer from picking-up, retraining, or transferring germs, bacteria, or viruses while wearing the hand barrier solution. The hand barrier system integrates three different components, to include: mixture, spraying, and curing.

Some embodiments of a method of forming a hand barrier include spraying a biodegradable antimicrobial solution onto a hand to provide a hand barrier that reduces microorganisms that are spread through touch. The hand barrier prevents a wearer from picking-up, retraining, or transferring germs, bacteria, or viruses while wearing the hand barrier solution. The hand barrier system integrates three different components, to include: mixture, spraying, and curing.

Some embodiments of a biodegradable antimicrobial solution are described. The solution is sprayed onto a hand to provide a hand barrier that reduces microorganisms that are spread through touch. The hand barrier prevents a wearer from picking-up, retraining, or transferring germs, bacteria, or viruses while wearing the hand barrier solution. The hand barrier system integrates three different components, to include: mixture, spraying, and curing.

Some embodiments of a device for forming a hand barrier from a biodegradable antimicrobial solution are described. The biodegradable antimicrobial solution is sprayed onto a hand to provide a hand barrier that reduces microorganisms that are spread through touch. The hand barrier prevents a wearer from picking-up, retraining, or transferring germs, bacteria, or viruses while wearing the hand barrier solution. The hand barrier system integrates three different components, to include: mixture, spraying, and curing.

Some embodiments form a liquid glove including biodegradable antimicrobial solution sprayed onto a hand to reduce microorganisms that are spread through touch. The solution forms a hand barrier that prevents a wearer from picking-up, retraining, or transferring germs, bacteria, or viruses while wearing the hand barrier solution. The hand barrier system integrates three different components, to include: mixture, spraying, and curing.

The embodiments described herein provide a biodegradable antimicrobial solution sprayed or otherwise dispensed onto the hand as a method, device and solution designed to reduce microorganisms that are often spread through touch. As a result, a user would not pick-up, retrain, or transfer germs, bacteria, or viruses while wearing embodiments of the hand barrier described herein. The hand barrier includes the integration between three different components, to include: mixture, spraying, and curing.

Some embodiments involve the use of one or more electronic or computing devices. Such devices typically include a processor, processing device, or controller, such as a general purpose central processing unit (CPU), a graphics processing unit (GPU), a microcontroller, a reduced instruction set computer (RISC) processor, an application specific integrated circuit (ASIC), a programmable logic circuit (PLC), a field programmable gate array (FPGA), a digital signal processing (DSP) device, and/or any other circuit or processing device capable of executing the functions described herein. The methods described herein may be encoded as executable instructions embodied in a computer readable medium, including, without limitation, a storage device and/or a memory device. Such instructions, when executed by a processing device, cause the processing device to perform at least a portion of the methods described herein. The above examples are exemplary only, and thus are not intended to limit in any way the definition and/or meaning of the term processor and processing device.

When introducing elements of the present invention or the preferred embodiment(s) thereof, the articles "a", "an", "the" and "the" are intended to mean that there are one or more of the elements. The terms "comprising", "including" and "having" are intended to be inclusive and mean that there may be additional elements other than the listed elements. Moreover, the use of "top", "bottom", "above", "below" and variations of these terms is made for convenience, and does not require any particular orientation of the components.

As various changes could be made in the above without departing from the scope of the invention, it is intended that all matter contained in the above description and shown in the accompanying drawings shall be interpreted as illustrative and not in a limiting sense.

What is claimed is:

1. A system for applying an antimicrobial barrier to a hand, the system comprising:
    a barrier precursor material;
    a reservoir for the barrier precursor material;
    a housing including at least one wall defining a cavity arranged to receive the hand of a person and an opening for the hand to be positioned through when the person is next to and on an exterior of the housing;
    a sensor configured to measure a length, a width, and a depth of a hand positioned adjacent the system;
    a controller connected to the sensor and configured to select a size and a shape of an antimicrobial barrier required to cover the hand based on information from the sensor;
    a dispenser connected to the reservoir and configured to dispense the barrier precursor material onto the hand of the person when the person is next to and on the exterior of the housing, wherein the controller is configured to control operation of the dispenser based on the size and shape of the antimicrobial barrier selected by the controller, wherein the barrier precursor material cures and adheres to the hand to form the antimicrobial barrier on the hand, wherein the antimicrobial barrier does not retain or transfer microorganisms from an object grasped by the hand, wherein the antimicrobial barrier has a first thickness in a first area of the hand and a second thickness in a second area of the hand, wherein the second thickness is larger than the first thickness to provide increased protection for the second area of the hand; and
    a user interface configured to send information to the controller, wherein the information includes at least one of user credentials or payment information, and wherein the controller is configured to compare the information received from the user interface to criteria stored in the controller and restrict access to the antimicrobial barrier based on the comparison.

2. The system of claim 1, wherein the housing further includes a door to selectively close the opening, wherein the door is in an open position when the dispenser dispenses the barrier precursor material onto the hand, and wherein the controller operates the door to restrict access to the cavity based on the comparison of the information received from the user interface and the criteria.

3. The system of claim 1, wherein the barrier precursor material comprises a solution comprising additives, an oil, an adhesive, and a solvent, and is free from skin irritants.

4. The system of claim 3, wherein the solution is configured to cure in two seconds or less after being dispensed onto the hand.

5. The system of claim 1, wherein the barrier precursor material is biodegradable.

6. The system of claim 1, wherein the dispenser includes at least one nozzle configured to spray the barrier precursor material onto the hand, a pump, and a motor, wherein the controller operates the motor and the pump to draw the barrier precursor material from the reservoir to supply the barrier precursor material to the nozzle to spray onto the hand.

7. The system of claim 1 further comprising an indicator connected to the reservoir and configured to provide an indication of an amount of barrier precursor material in the reservoir.

8. The system of claim 1, wherein the antimicrobial barrier covers the entirety of the hand.

9. The system of claim 1, wherein the controller is configured to determine if the hand is removed from the cavity before the dispenser dispenses the barrier precursor material onto the hand.

10. The system of claim 1, wherein the sensor is configured to detect and scan the hand, and wherein the controller is configured to determine if the hand is ready for the dispenser to dispense the barrier precursor material.

11. The system of claim 1, wherein the sensor is configured to generate an image of the hand, and wherein the controller is configured to determine the size and shape of the antimicrobial barrier to cover the hand based on the image of the hand.

12. The system of claim 1, wherein the controller is configured to:
    determine if the barrier precursor material is cured to form the antimicrobial barrier before the hand is moved away from the dispenser; and
    provide an alert if the hand is moved away from the dispenser before the barrier precursor material is cured.

13. The system of claim 1, wherein the antimicrobial barrier is transparent.

14. The system of claim 1, wherein the first thickness and the second thickness are less than 1 millimeter.

15. A method of applying an antimicrobial barrier to a hand, said method comprising:
    receiving a user input at a user interface configured to send information to a controller, wherein the controller is configured to compare the information received from the user interface to criteria stored in the controller and restrict access to the antimicrobial barrier based on the comparison;
    detecting a hand positioned through an opening defined by at least one wall of a housing, the housing including the at least one wall defining a cavity arranged to receive the hand of a person and the opening for the hand to be positioned through when the person is next to and on an exterior of the housing, wherein a dispenser is connected to a reservoir of barrier precursor material and arranged to dispense the barrier precursor material onto the hand of the person when the person is next to and on the exterior of the housing;

measuring, via a sensor, a length, a width, and a depth of the hand;

selecting, via controller connected to the sensor, a size and a shape of an antimicrobial barrier to cover the hand based on information from the sensor;

dispensing, via the dispenser, the barrier precursor material onto the hand positioned adjacent the dispenser, wherein the controller is configured to control operation of the dispenser based on the size and shape of the antimicrobial barrier determined by the controller, wherein the barrier precursor material cures and adheres to the hand to form an antimicrobial hand barrier on the hand after the barrier precursor material is dispensed onto the hand by the dispenser, wherein the antimicrobial hand barrier does not retain or transfer microorganisms from an object grasped by the hand, wherein the antimicrobial barrier has a first thickness in a first area of the hand and a second thickness in a second area of the hand, wherein the second thickness is larger than the first thickness to provide increased protection for the second area of the hand;

determining if the barrier precursor material is cured to form the antimicrobial hand barrier before the hand is moved away from the dispenser; and providing an alert if the hand is moved away from the dispenser before the barrier precursor material is cured.

16. The method of claim 15 further comprising providing an indication when the barrier precursor material has cured to form the antimicrobial barrier on the hand, wherein the barrier precursor material is configured to cure in two seconds or less after being dispensed onto the hand.

17. The method of claim 15, wherein dispensing the barrier precursor material onto the hand comprises spraying the barrier precursor material onto the hand using at least one nozzle.

18. The method of claim 17, wherein the at least one nozzle comprises a plurality of nozzles positioned on opposite sides of the hand, wherein spraying the barrier precursor material onto the hand using the at least one nozzle includes spraying the barrier precursor material onto opposite sides of the hand simultaneously using the plurality of nozzles.

19. A system for applying an antimicrobial barrier to a hand, the system comprising:

a reservoir;

a housing including at least one wall defining a cavity arranged to receive the hand of a person and an opening for the hand to be positioned through when the person is next to and on an exterior of the housing;

a sensor configured to measure a length, a width, and a depth of hand positioned in the cavity;

a controller connected to the sensor and configured to select a size and a shape of an antimicrobial barrier required to cover the hand based on information from the sensor;

a user interface configured to send information to the controller, wherein the controller is configured to compare the information received from the user interface to criteria stored in the controller and restrict access to the antimicrobial barrier based on the comparison;

a dispenser connected to the reservoir and the controller; and an antimicrobial barrier configured to adhere to a hand, wherein the antimicrobial barrier has the size and the shape selected by the controller to cover the hand based on information from the sensor, wherein the antimicrobial barrier does not retain or transfer microorganisms from an object grasped by the hand, wherein the antimicrobial barrier has a first thickness in a first area of the hand and a second thickness in a second area of the hand, wherein the second thickness is larger than the first thickness to provide increased protection for the second area of the hand, wherein the hand barrier is transparent, and wherein the first thickness and the second thickness are less than 1 millimeter, wherein the dispenser is arranged to dispense a barrier precursor material or the antimicrobial barrier onto the hand of the person when the person is next to and on the exterior of the housing.

20. The system of claim 19, wherein the housing further includes a door to selectively close the opening, wherein the controller operates the door to restrict access to the cavity based on the comparison of the information received from the user interface and the criteria.

* * * * *